US008653043B2

(12) United States Patent
Goff et al.

(10) Patent No.: US 8,653,043 B2
(45) Date of Patent: *Feb. 18, 2014

(54) ENHANCED NEOGLYCOSIDES THROUGH NEOGLYCOSYLATION AND METHODS OF USE THEREOF

(75) Inventors: Randal D. Goff, Madison, WI (US); Jon Scott Thorson, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 177 days.

This patent is subject to a terminal disclaimer.

(21) Appl. No.: 13/143,639

(22) PCT Filed: Jan. 7, 2010

(86) PCT No.: PCT/US2010/020300
§ 371 (c)(1),
(2), (4) Date: Jul. 7, 2011

(87) PCT Pub. No.: WO2010/080863
PCT Pub. Date: Jul. 15, 2010

(65) Prior Publication Data
US 2012/0108530 A1 May 3, 2012

Related U.S. Application Data

(60) Provisional application No. 61/143,061, filed on Jan. 7, 2009.

(51) Int. Cl.
*A61K 31/70* (2006.01)
*C07H 5/06* (2006.01)
(52) U.S. Cl.
USPC ............................................ 514/42; 536/29.1
(58) Field of Classification Search
None
See application file for complete search history.

(56) References Cited

U.S. PATENT DOCUMENTS 7,160,867 B2   1/2007   Abel et al.
8,372,808 B2 *  2/2013   Messing et al. ............... 514/12.1

FOREIGN PATENT DOCUMENTS

WO    2008/067039    6/2008

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
The International Search Report as mailed on Mar. 10, 2010 for International Application No. PCT/US2010/20300.

Goff, et al., Enhancing the Divergent Activities of Betulinic Acid via Neoglycosylation, Org. Lett., 11(2), pp. 461-464, 2009, Abstract; p. 462-p. 464; Scheme 2; Fig. 2; Publication Date (Web): Dec. 22, 2008.
Ahmed, et al., Colchicine Glycorandomization Influences Cytotoxicity and Mechanism of Action, J. Am. Chem. Soc., 2006, 128:14224-14225.
Aiken, et al., Betulinic Acid Derivatives as HIV-1 Antivirals, Trends Mol. Med., 2005, 11:31-36.
Blanchard, et al., Enzymatic Tools for Engineering Natural Product Glycosylation, Curr. Opin. Chem. Biol., 2006, 10:263-271.
Butler, Natural Products to Drugs: Natural Product-Derived Compounds in Clinical Trials, Nat. Prod. Rep., 2008, 25:475-516.
Carrasco, et al., Synthesis of Neoglycopeptides by Chemoselective Reaction of Carbohydates with Peptides Containing a Novel N'-methyl-aminooxy amino acid, Tetrahedron Lett., 2002, 43:5727-5729.
Carrasco, et al., Synthesis of N-Fmoc-O-(N'-Boc-N'-methyl)-aminohomoserine, an Amino Acid for the Facile Preparation of Neoglycopeptides, J. Org. Chem., 2003, 68:195-197.
Carrasco, et al., A Versatile Set of Aminooxy Amino Acids for the Synthesis of Neoglycopeptides, J. Org. Chem., 2003, 68:8853-8858.
Carrasco, et al., 2-(N-Fmoc)-3-(N-Boc-N-Methoxy)-Diaminopropanoic Acid, an Amino Acid for the Synthesis of Mimics of O-Linked Glycopeptides, Biopolymers (Peptide Science), 2006, 84:414-420.
Chintharlapalli, et al., Betulinic Acid Inhibits Prostate Cancer Growth through Inhibition of Specificity Protein Transcription Factors, Cancer Res., 2007, 67:2816-2823.
Cichewicz, et al., Chemistry, Biological Activity, and Chemotherapeutic Potential of Betulinic Acid for the Prevention and Treatment of Cancer and HIV Infection, Medicinal Research Reviews, 2004, 24:90-114.
Deorukhkar, et al., Back to Basics: How Natural Products Can Provide the Basis for New Therapeutics, Expert Opinion on Investigational Drugs, 2007, 16(11):1753-1773.
Fulda, Betulinic Acid: A New Cytotoxic Agent Against Malignant Brain-Tumor Cells, Int. J. Cancer, 1999, 82:435-441.
Fulda, Betulinic Acid for Cancer Treatment and Prevention, Int. J. Mol. Sci., 2008, 9:1096-1107.
Gauthier, et al., Glycosidation of Lupane-Type Triterpenoids as Potent in Vitro Cytotoxic Agents, Bioorganic & Medicinal Chemistry, 2006, 14:6713-6725.
Ghiorghis, et al., In Vitro Antineoplastic Activity of C7-Substituted Mitomycin C Analogues MC-77 and MC-62 Against Human Breast-Cancer Cell Lines, Cancer Chemotherapy and Pharmacology, 1992, 29(4):290-296.
Griffith, et al., 'Sweetening' Natural Products via Glycorandomization, Curr. Opin. Biotechnol., 2005, 16:622-630.
Griffith, et al., Model for Antibiotic Optimization via Neoglycosylation: Synthesis of Liponeoglycopeptides Active Against VRE, J. Am. Chem. Soc., 2007, 129:8150-8155.
Imbert, Discovery of Podophyllotoxins, Biochimie, 1998, 80:207-222.

(Continued)

*Primary Examiner* — Traviss C McIntosh, III
(74) *Attorney, Agent, or Firm* — Quarles & Brady LLP

(57) ABSTRACT

Using neoglycosylation, the impact of differential glycosylation upon the divergent anticancer and anti-HIV properties of the triterpenoid betulinic acid (BA) was examined. Each member from a library of 37 differentially glycosylated BA variants was tested for anticancer and anti-HIV activities. Enhanced analogs for both desired activities were discovered with the corresponding antitumor or antiviral enhancements diverging, based upon the appended sugar, into two distinct compound subsets.

16 Claims, 14 Drawing Sheets

(56) References Cited

OTHER PUBLICATIONS

Kashiwada, et al., Synthesis and Anti-HIV Activity of 3-Alkylamido-3-deoxy-betulinic Acid Derivatives, Chem. Pharm. Bull., 2000, 48:1387-1390.

Kashiwada, et al., 3,28-Di-0-(dimethylsuccinyl)-betulin Isomers as Anti-HIV Agents, Bioorganic & Medicinal Chemistry Letters, 2001, 11:183-185.

Kim, et al., A Concise Semi-Synthetic Approach to Betulinic Acid from Betulin, Synthetic Communications, 1997, 27:1607-1612.

Kim, et al., Synthesis of Betulinic Acid Derivatives with Activity Against Human Melanoma, Bioorganic & Medicinal Chemistry Letters, 1998, 8:1707-1712.

Kren, et al., Sweet Antibiotics—The Role of Glycosidic Residues in Antibiotic and Antitumor Activity and their Randomization, FEMS Microbiol. Rev., 2008, 32:858-889.

Langenhan, et al., Neoglycorandomization and Chemoenzymatic glycorandomization: Two Complementary Tools for Natural Product Diversification, J. Nat. Prod., 2005, 68:1696-1711.

Langenhan, et al., Recent Carbohydrate-Based Chemoselective Ligation Applications, Current Organic Synthesis, 2005, 2:59-81.

Langenhan, et al., Enhancing the Anticancer Properties of Cardiac Glycosides by Neoglycorandomization, Proc. Natl. Acad. Sci. U.S. A., 2005, 102:12305-12310.

Langenhan, et al., Modifying the Glycosidic Linkage in Digitoxin Analogs Provides Selective Cytotoxins, Bioorganic & Medicinal Chemistry Letters, 2008, 18:670-673.

Li, et al., PA-457: A Potent HIV Inhibitor that Disrupts Core Condensation by Targeting a Late Step in Gag Processing, Proc. Nat. Acad. Sci. U.S.A., 2003, 100:13555-13560.

Liu, et al., Synthesis of 2'-paclitaxel methyl 2-glucopyranosyl succinate for Specific Targeted Delivery to Cancer Cells, Bioorganic & Medicinal Chemistry Letters, 2007, 17:617-620.

Nicotra, et al., Chemoselective Neoglycosylation, Adv. Carb. Chem. Biochem., 2008, 61:353-410.

Peri, et al., Chemo- and Stereoselective Glycosylation of Hydroxylamino Derivatives: A Versatile Approach to Glycoconjugates, Tetrahedron, 1998, 54:12269-12278.

Peri, et al., Solution and Solid-Phase Chemoselective Synthesis of (1-6)-amino(methoxy) Di- and Trisaccharide Analogues, Chem. Commun., 2002, 1504-1505.

Peri, et al., Extending Chemoselective Ligation to Sugar Chemistry: Convergent Assembly of Bioactive Neoglycoconjugates, Mini Reviews in Medicinal Chemistry, 2003, 3(7):651-658.

Peri, et al., Synthesis and Conformational Analysis of Novel N(OCH3)-Linked Disaccharide Analogues, Chem. Eur. J., 2004, 10:1433-1444.

Peri, et al., Chemoselective Ligation in Glycochemistry, Chem. Commun., 2004, 623-627.

Ptak, et al., Inhibition of Human Immunodeficiency Virus Type 1 Replication in Human Cells by Debio-025, a Novel Cyclophilin Binding Agent, Antimicrobial Agents and Chemotherapy, 2008, 52:1302-1317.

Saladino, et al., Advances and Challenges in the Synthesis of Highly Oxidised Natural Phenols with Antiviral, Antioxidant and Cytotoxic Activities, Current Medicinal Chemistry, 2008, 15(15):1500-1519.

Salas, et al., Engineering the Glycosylation of Natural Products in Actinomycetes, Trends Microbiol., 2007, 15:119-232.

Sami, et al., Pharmacological Properties of the Ubiquitous Natural Product Betulin, Eur. J. Pharm. Sci., 2006, 29:1-13.

Schmidt, et al., Betulinic Acid Induces Apoptosis in Human Neuroblastoma Cell Lines, Eur. J. Cancer, 1997, 33:2007-2010.

Thibeault, et al., Synthesis and Structure-Activity Relationship Study of Cytotoxic Germanicane- and Lupane-type 3B-O-monodesmosidic Saponins Starting from Betulin, Bioorganic & Medicinal Chemistry, 2007, 15:6144-6157.

Thibodeaux, et al., Unusual Sugar Biosynthesis and Natural Product Glycodiversification, Nature, 2007, 446:1008-1016.

Thorson, et al., Nature's Carbohydrate Chemists: The Enzymatic Glycosylation of Bioactive Bacterial Metabolites, Current Organic Chemistry, 2001, 5(2):139-167.

Udenigwe, et al., Potential of Resveratrol in Anticancer and Anti-Inflammatory Therapy, Nutr. Rev., 2008, 66:445-454.

Weymouth-Wilson, The Role of Carbohydrates in Biologically Active Natural Products, Natural Product Reports, 1997, 14:99-110.

Yogeeswari, et al., Betulinic Acid and Its Derivatives: A Review on Their Biological Properties, Current Medicinal Chemistry, 2005, 12:657-666.

Promega Corporation, Technical Bulletin, CellTiter 96 AQueous One Solution Cell Proliferation Assay, Instructions for Use of Products G3580, G3581 and G3582, Part # TB245, Revised Jun. 2009.

* cited by examiner

ENHANCED NEOGLYCOSIDES THROUGH NEOGLYCOSYLATION AND METHODS OF USE THEREOF

CROSS-REFERENCE TO RELATED APPLICATIONS

This application claims priority to U.S. Provisional Application No. 61/143,061 filed Jan. 7, 2009. The present application represents the U.S. National State of International Application No. PCT/US2010/020300, filed Jan. 7, 2010. The foregoing applications are incorporated herein by reference in their-entirety.

STATEMENT REGARDING FEDERALLY SPONSORED RESEARCH OR DEVELOPMENT

This invention was made with United States government support awarded by the following agency: NIH CA113297 The United States government has certain rights in this invention.

FIELD OF THE INVENTION

The invention relates generally to methods of enhancing the inherent properties of neoglycosides through neoglycosylation and uses thereof.

BACKGROUND OF THE INVENTION

The sugars attached to pharmaceutically important natural products often dictate key pharmacological properties and/or molecular mechanisms of action. While there is precedent for improving non-glycosylated natural product-based therapeutics via glycoconjugation with, among others, colchicine, mitomycin, podophyllotoxin, rapamycin, or taxol, studies designed to systematically understand and/or exploit the role of carbohydrates in drug discovery are often limited by the availability of practical synthetic and/or biosynthetic tools.

Among the contemporary options to address this limitation, neoglycosylation takes advantage of a chemoselective reaction between free reducing sugars and Nmethoxyamino-substituted acceptors. This reaction has enabled the process of 'neoglycorandomization' wherein alkoxyamine-appended natural product-based drugs are differentially glycosylated with a wide array of natural and unnatural reducing sugars.

Neoglycorandomization has led to increases in anticancer efficacy of the cardenolide digitoxin, mechanistic alteration and improvements in the synergistic effects of the non-glycosylated alkaloid colchicine, and enhancements in the potency of the glycopeptide vancomycin against antibiotic resistant organisms. Importantly, although many natural products are known to exhibit multiple, diverse biological activities, neoglycorandomization to date has focused upon natural product-based drugs with predominately singular, distinct mechanisms of action.

Cancer affects approximately 20 million adults and children worldwide, with more than 9 million new cases diagnosed annually (International Agency for Research on Cancer). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section 9). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects.

With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multidrug resistance.

Therefore, there exists a significant need in the art for novel compounds and compositions, and methods of preparing the same that are useful for treating cancer or neoplastic disease with reduced or without the aforementioned side effects. Further, there is a need for cancer treatments that provide cancer-cell-specific therapies with increased specificity and decreased toxicity.

SUMMARY OF THE INVENTION

The present invention provides a novel neoglycoside having the chemical structure:

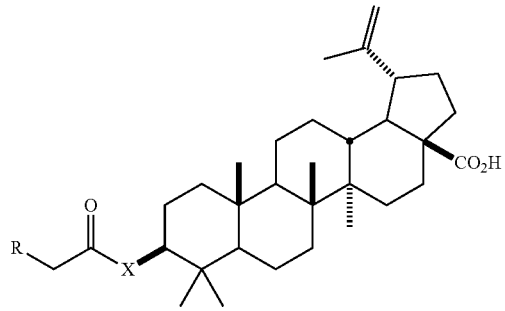

wherein X represents either O or NH, and wherein R is an amine group having the nitrogen atom covalently bonded to both a methoxy moiety ($CH_3O$—) and a reducing sugar.

In alternate embodiments, R is chosen from the group consisting of: D-alloside; L-alloside; D-altroside; L-altroside; D-arabinoside; L-arabinoside; D-digitoxoside; D-fucoside; L-fucoside; D-galactoside; L-galactoside; D-galacturonide; D-GalNAc; D-glucoside; L-glucoside; D-glucoside, 2-fluoro; D-glucoside, 3-deoxy; D-glucoside, 6-deoxy; D-glucoside, 3-O-methyl; D-glucuronide; D-glucurono-6,3-lactonide; D-lyxoside; L-lyxoside; D-mannoside; L-mannoside; D-ManNAc; L-rhamnoside; D-riboside; L-riboside; D-taloside; D-xyloside; and L-xyloside.

In an alternate embodiment, the present invention provides a library of neoglycosides comprising at least two of the neoglycosides described above.

In an alternate embodiment, the present invention provides a composition comprising one or more of the neoglycosides described above, or a pharmaceutically acceptable salt, ester, or prodrug thereof, and a pharmaceutically acceptable carrier.

In an alternate embodiment, the present invention provides a method of treating a subject having cancer cells comprising the step of contacting the cancer cells with an effective amount of the neoglycoside as described above, or a pharmaceutically acceptable salt, ester, or prodrug thereof. In one embodiment, the step of contacting the cancer cells with an effective amount of the neoglycoside, pharmaceutically acceptable salt, ester, or prodrug thereof is accomplished by administering to the subject the composition comprising one or more of the neoglycosides described above, or a pharmaceutically acceptable salt, ester, or prodrug thereof, and a pharmaceutically acceptable carrier.

In an alternate embodiment, the present invention provides a method of treating HIV infection comprising the step of administering to a subject having an HIV infection an effective amount of the neoglycoside as described above, or a pharmaceutically acceptable salt, ester, or prodrug thereof. In one embodiment, the step of administering an effective amount of the neoglycoside, pharmaceutically acceptable salt, ester, or prodrug thereof is accomplished by administering to the subject the composition comprising one or more of the neoglycosides described above, or a pharmaceutically acceptable salt, ester, or prodrug thereof, and a pharmaceutically acceptable carrier.

In an alternate embodiment, the present invention provides a method of making a neoglycoside comprising the steps of: (a) contacting a parent compound having a hydroxyl group with chloroacetyl chloride, DMAP, iodide ion, and methoxyamine (MeOHN$_2$) to produce an aglycon; and (b) contacting the aglycon produced in step (a) with one or more reducing sugars. In one embodiment, the parent compound is betulinic acid and the reducing sugar is selected from the group consisting of D-allose, L-allose, D-altrose, L-altrose, D-arabinose, L-arabinose, D-digitoxose, D-fucose, L-fucose, D-galactose, L-galactose, D-galacturone, D-GalNAc, D-glucose, L-glucose, 2-fluoro-D-glucose, 3-deoxy-D-glucose, 6-deoxy-D-glucose, 3-O-methyl-D-glucose, D-glucurone, D-glucurono-6,3-lacone, D-lyxose, L-lyxose, D-mannose, L-mannose, D-manNAc, L-rhamnose, D-ribose, L-ribose, D-talose, D-xylose, or L-xylose.

In one embodiment, the contacting is performed at a temperature from about 40 degrees Celsius to about 60 degrees Celsius, and the step of contacting the aglycon produced in step (a) with one or more reducing sugars is performed in the presence of a mixture of Methanol and $CH_2Cl_2$. In one embodiment, the ratio of Methanol to $CH_2Cl_2$ in the mixture is about 6:1.

The present invention also provides a novel neoglycoside produced by the method described above useful in the treatment of cancer and/or HIV infection alone or as a medicament.

Other objects, features and advantages of the present invention will become apparent after review of the specification, claims and drawings.

DETAILED DESCRIPTION OF THE INVENTION

Figure 1:
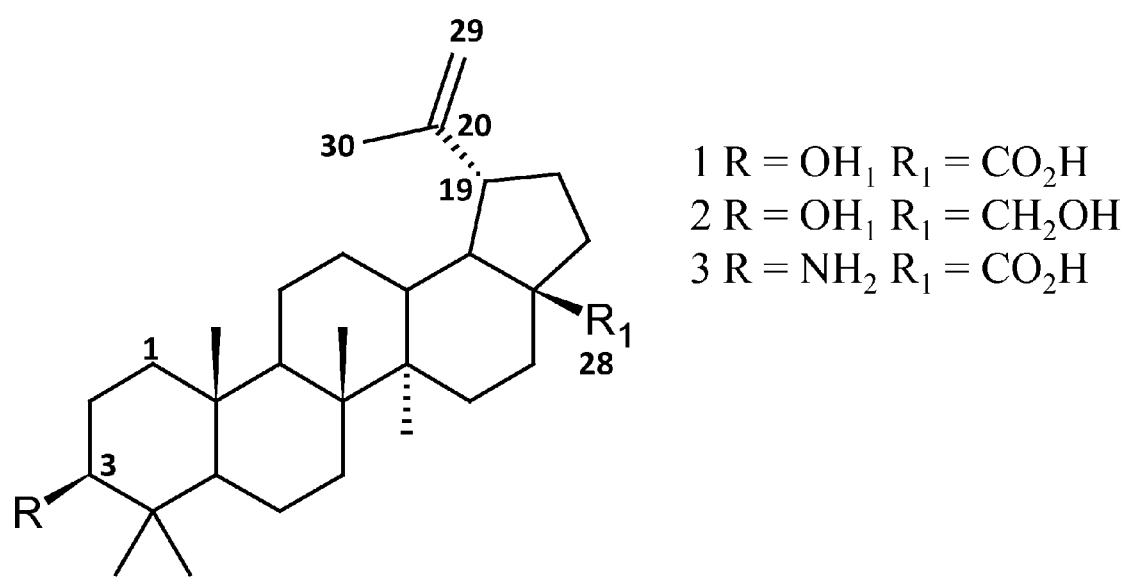
FIG. 1. Structure of betulinic acid (1), betulin (2) and 3-aminobetulinic acid (3).

Here, the inventors demonstrate a versatile method for enhancing the properties of neoglycosides through neoglycosylation. Neoglycosylation has enabled the study of the influence of glycodiversification upon the divergent activities of neoglycosides, including, without limitation, neoglycosides such as betulinic acid (BA). Here, the inventors reveal distinct sets of sugars to discretely augment either the anticancer or anti-HIV activity of BA. While the anticancer or anti-HIV activities of BA neoglycosides were predominately dictated by the appended sugar, the nature of the alkoxyamine handle connection to the scaffold (i.e., ester versus amide) also appeared to contribute to the divergence of the mode of action. As a first application of neoglycosylation toward a triterpenoid and the first installation of the methoxyamine handle via a linker strategy, the present invention also significantly extends the utility of neoglycosylation as a tool for natural product glycodiversification.

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

In the present invention, the inventors provide a novel method of enhancing the inherent properties of a neoglycoside through chemoselective "neoglycosylation" chemistry. The enhanced neoglycosides can then be used to more effectively treat patients suffering from such things as cancer, HIV and more. While the following description refers to methods of enhancing the neoglycoside betulinic acid (BA), it is understood that the methods of the present invention may be used with all neoglycosides.

To assess the impact of differential glycosylation upon a natural product with known multiple activities, the inventors selected the lupane-type triterpernoid betulinic acid (BA, 1) as a model (FIG. 1). BA, and its reduced form (betulin, 2), exhibit a wide variety of biological functions, the most prevalent of which are anticancer and anti-HIV activities. In cancer cells, BA induces apoptosis through multiple mechanisms, including disruption of the mitochondrial membrane potential and suppression of vascular endothelial growth factor and surviving proteins.

Although the exact mechanism of BA anti-HIV activity has yet to be elucidated, many BA analogs disrupt viral fusion to host cells through interference with the gp41 viral glycoprotein or function as inhibitors of the late stage of capsid protein maturation.

While BA derivatization (primarily at C3 and/or C28) has yielded anti-HIV or antitumor enhancements, few glycosylated BAs have been pursued or studied. Studies by Pichette and coworkers revealed that the attachment of saccharides at C3 moderately improved the antiproliferative activity (up to 4-fold) and selectivity of BA in a sugar-dependent dependent manner. However, while the methods of the present invention are applicable to all neoglycosides, only D-Ara, D-Gal, D-Glc, D-Man, L-Rha, and D-Xyl were employed herein.

Figure 2:
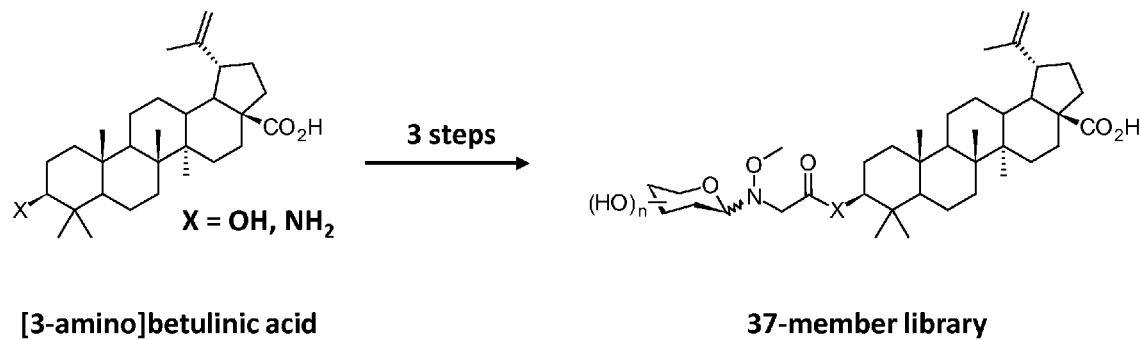
FIG. 2. Neoglycosylation of 3-amino betulinic acid into a 37-member library.
Figure 3:
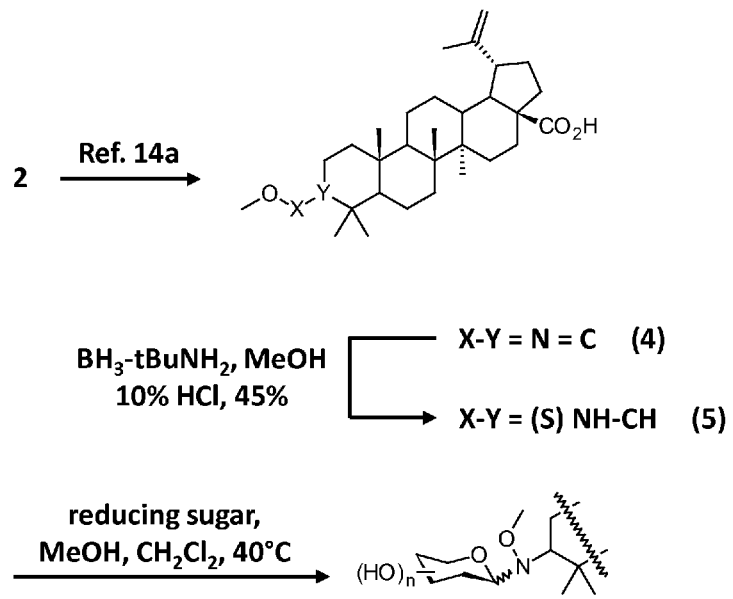
FIG. 3. Scheme 1—the attempted direct neoglycosylation of betulinic acid.

To more systematically assess the impact of BA glycosylation upon both anticancer activity/selectivity and antiviral activity in parallel, herein the inventors report the synthesis and anticancer/antiviral activities of a 37-member library of BA C3-neoglycosides (FIG. 2). The inventors findings indicate that groups of BA derivatives with improved antitumor or antiviral properties are divergent and thus represent unique subsets of compounds. The initial strategy for methoxyamine handle installation at C3 involved reductive amination of imine 4 (created from 2) using BH3.t-BuNH2 to give a 3:1 ratio of desired to undesired diastereomers (5) (FIG. 3). However, attempts to neoglycosylate 5 failed, possibly due to steric interference of the adjacent C4 dimethyl substitution.

Consistent with this, aglycon 5 was also resistant to acetylation in the presence of acetic anhydride and DMAP in refluxing pyridine. Previously, colchicine neoglycosylation was enabled by replacing the natural colchicine N-acetyl group with N—(N'-methoxyglycine). While not a direct neoglycosylation of the terpene scaffold, the inventors postulated that a similar methoxyglycine handle would distance the hindered BA C4 quaternary center from the requisite neoglycosylation alkoxyamine.

Figure 4:
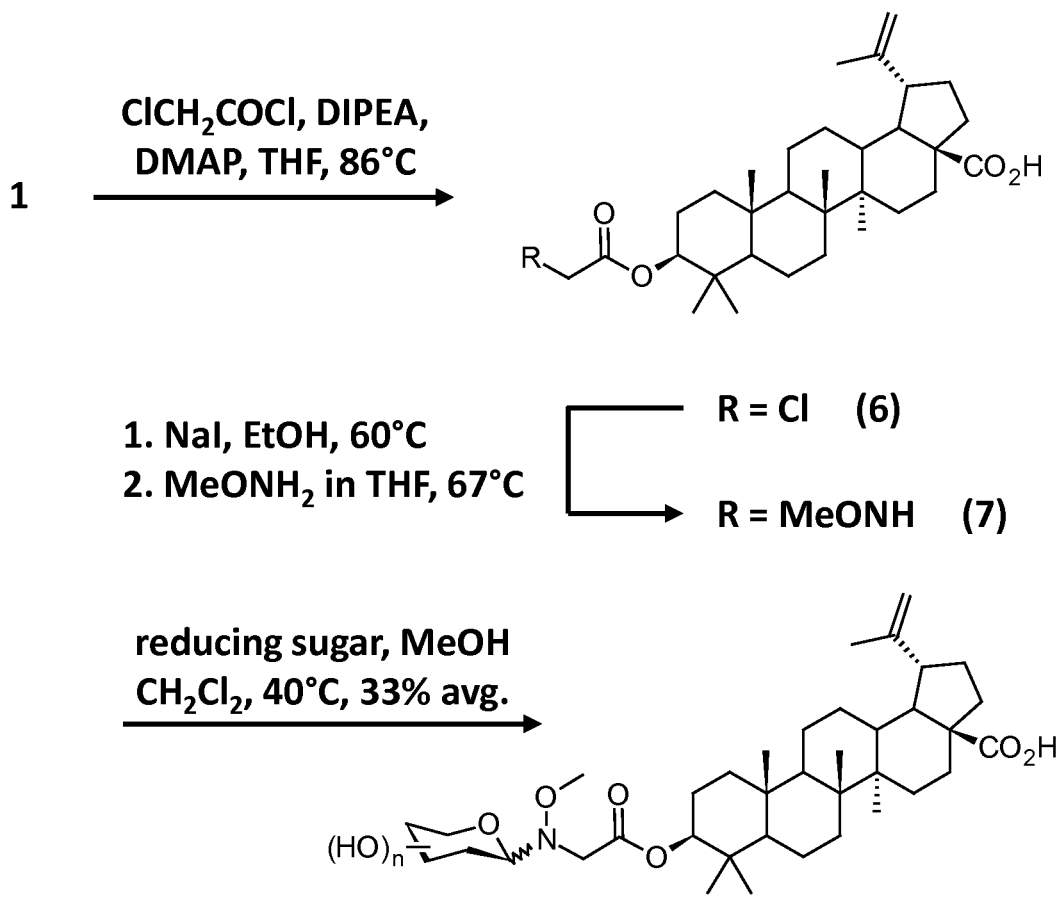
FIG. 4. Scheme 2—they synthesis of betulinic acid neoglycosides.

Toward this goal, 1 (prepared in three steps from 2) was esterified at the C3 hydroxyl group using chloroacetyl chloride in the presence of DMAP. Under Finklestein conditions, the chloride (6) was exchanged with iodide to facilitate the SN2 displacement by methoxyamine in the same reaction vessel (FIG. 4). This three step procedure provided aglycon 7 in good yield (58%), a marked improvement over the previous colchicine N'-methoxyglycine incorporation strategy (eight steps, 40% yield).[2] Optimal neoglycosylation conditions of 7 were identified using L-ribose (see Table 1), validating, for the first time, an ester-linked neoglycosylation handle.

TABLE 1

Optimization of Neoglycosylation Constants

| entry | L-ribose(eq.) | solvent[a] | % yield |
|---|---|---|---|
| 1 | 5 | 3:1 DMF:HOAc | 36% |
| 2 | 2 | 6:1 MeOH:$CH_2Cl_2$ | 17% |
| 3 | 3 | 6:1 MeOH:$CH_2Cl_2$ | 48% |
| 4 | 5 | 6:1 MeOH:$CH_2Cl_2$ | 49% |

[a]Concentration of 7 at 90 mM

Figure 5:
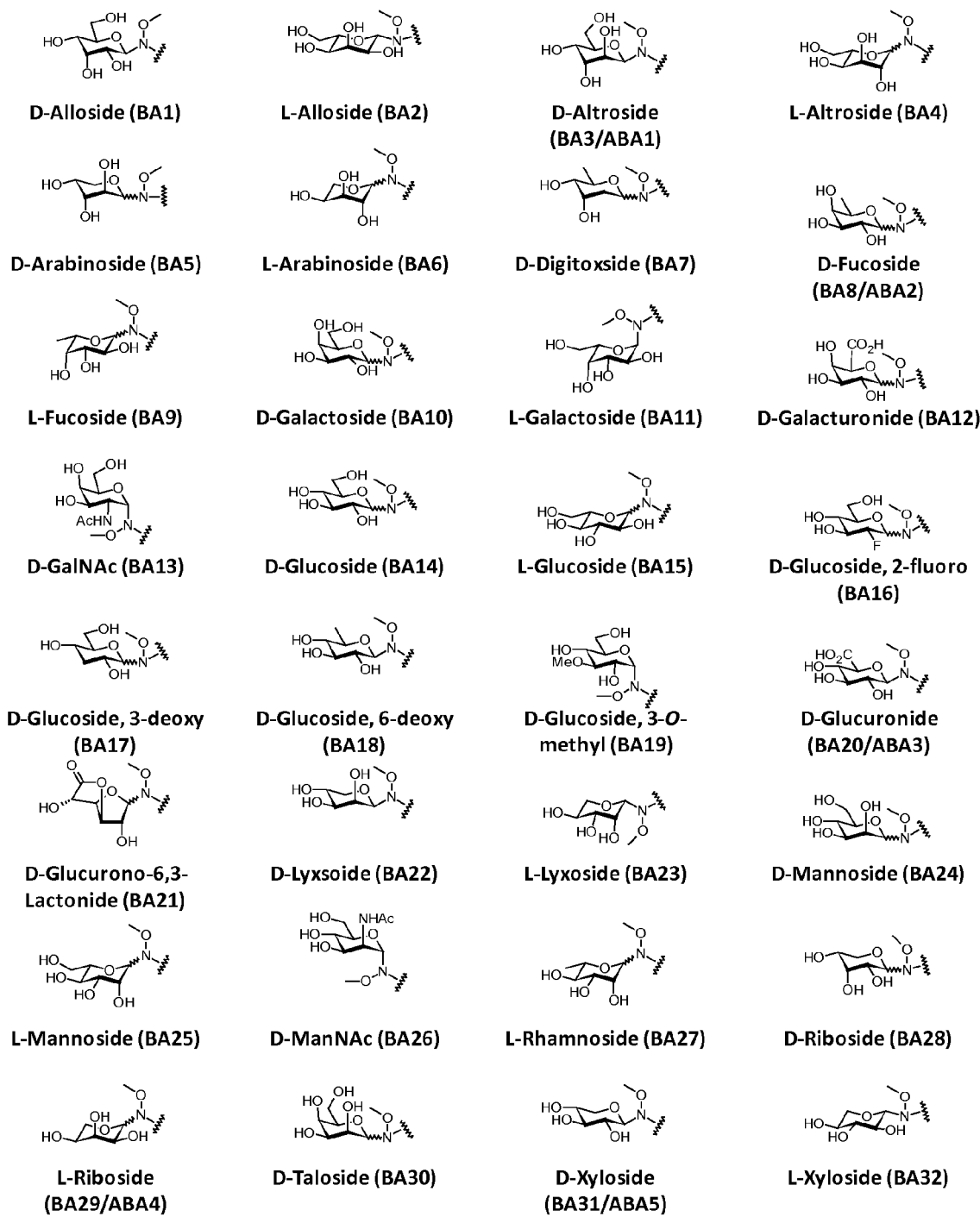
FIG. 5. Betulinic acid neoglycoside library.

In contrast to the typical DMF:acetic acid (3:1) neoglycosylation solvent system, the inventors have found a ratio of 6:1 MeOH:$CH_2Cl_2$ to be optimal. Notably distinct from prior neoglycosylation applications, an external proton source was also unnecessary, likely due to the intrinsic carboxylic acid of 7. Production of the corresponding neoglycoside library (BA1-32, see FIG. 5) employed similar conditions (90 μM aglycon, 3 eq. sugar, 40° C., 48 hr), with an average isolated yield of 33%.

Unlike previously reported libraries that revealed a predominance of α-anomers, the anomeric bias in the context of BA neoglycosylation was not as strong (see Table 2). The cytotoxicity of the library members was assessed in seven human cancer cell lines representing a broad range of carcinomas including breast, colorectal, CNS, lung and prostate.

TABLE 2

$^1$HNMR Anomeric Proton and ESI-HRMS Characterization [a]

| entry | neoglycoside | α-anomeric H1 (ppm) | J(Hz) | β-anomeric H1 (ppm) | J(Hz) | α:β ratio | HRMS (EST) m/z measured | calculated |
|---|---|---|---|---|---|---|---|---|
| BA1 | D-Alloside | not observed | | 4.50 | 9.2 | β only | 728.4365[b] | 728.4344 |
| BA2 | L-Alloside | not observed | | 4.50 | 9.2 | β only | 728.4382[b] | 728.4344 |
| BA3 | D-Altroside | 4.21-4.16[c] | n/d[d] | 4.57 | 4.4 | n/d | 728.4323[b] | 728.4344 |
| BA4 | L-Altroside | 4.25-4.16[c] | n/d | 4.55 | 4.4 | n/d | 728.4364[b] | 728.4344 |
| BA5 | D-Arabinoside | 4.11 | 8.4 | 4.58 | 5.1 | 1:1 | 698.4227[b] | 698.4239 |

TABLE 2-continued

¹HNMR Anomeric Proton and ESI-HRMS Characterization [a]

| | | | | | | | | |
|---|---|---|---|---|---|---|---|---|
| BA6 | L-Arabinoside | 4.04 | 8.6 | 4.50 | 5.0 | 1:1 | 674.4244[b] | 674.4274 |
| BA7 | D-Digitoxoside | | 4.66-4.64[f] | | | 1 anomer | 696.4484[b] | 686.4446 |
| BA8 | D-Fucoside | 4.48 | 5.2 | 4.08 | | 1:2 | 712.4409[b] | 712.4395 |
| BA9 | L-Fucoside | 4.51 | 5.2 | 4.10 | 8.6 | 1:2 | 688.4423[b] | 688.4430 |
| BA10 | D-Galactoside | | 4.60-4.53[f] | | 8.6 | 1 anomer | 728.4329[b] | 728.4344 |
| BA11 | L-Galactoside | 4.55 | 5.4 | not observed | | α only | 728.4343[b] | 728.4344 |
| BA12 | D-Galacturonide | | 4.27-4.21[f] | | | 1 anomer | 742.4128[b] | 742.4137 |
| BA13 | D-GalNAc | 4.65 | 5.2 | not observed | | α only | 769.4601[b] | 769.4610 |
| BA14 | D-Glucoside | 4.65-4.54[c] | n/d | 4.17 | 8.6 | n/d | 728.4346[b] | 728.4344 |
| BA15 | L-Glucoside | 4.65-4.54[c] | n/d | 4.19 | 8.8 | n/d | 728.4357[b] | 728.4344 |
| BA16 | D-Glucoside, 2-fluoro | | 4.65-4.63[f] | | | 1 anomer | 730.4287[b] | 730.4301 |
| BA17 | D-Glucoside, 3-deoxy | 4.54 | 1.4 | 4.42 | 5.7 | 1:3 | 712.4434[b] | 712.4395 |
| BA18 | D-Glucoside, 6-deoxy | not observed | | 4.12 | 8.9 | β only | 712.4420[b] | 712.4395 |
| BA19 | D-Glucoside, 3-O—Me | 4.67 | 3.0 | not observed | | α only | 742.4504[b] | 742.4501 |
| BA20 | D-Glucuronide | not observed | | 4.25 | 8.7 | β only | 742.4143[b] | 742.4137 |
| BA21 | D-Glucuronolactonide | | 4.89-4.87[f] | | | 1 anomer | 724.4033[b] | 724.4031 |
| BA22 | D-Lyxoside | not observed | | 4.46 | 8.7 | β only | 698.4268[b] | 698.4239 |
| BA23 | L-Lyxoside | not observed | | 4.44 | 8.6 | β only | 698.4243[b] | 698.4239 |
| BA24 | D-Mannoside | 4.37 | 1.8 | 4.65-4.62[c] | n/d | n/d | 728.4318[b] | 728.4344 |
| BA25 | L-Mannoside | 4.43 | 1.7 | 4.65-4.62[c] | n/d | n/d | 728.4376[b] | 728.4344 |
| BA26 | D-ManNAc | 4.64 | 5.2 | not observed | | α only | 769.4597[b] | 769.4610 |
| BA27 | L-Rhamnoside | 4.37 | 3.1 | 4.59 | 1.7 | 5.1 | 712.4376[b] | 712.4395 |
| BA28 | D-Riboside | 4.63 | 3.5 | 4.40 | 8.7 | 1.2 | 698.4232[b] | 698.4239 |
| BA29 | L-Riboside | 4.61 | 3.8 | 4.39 | 8.8 | 1.2 | 698.4232[b] | 698.4239 |
| BA30 | D-Taloside | | 4.65-4.63[f] | | | 1 anomer | 706.4500[b] | 706.4525 |
| BA31 | D-Xyloside | not observed | | 4.08 | 8.7 | β only | 698.4257[b] | 698.4239 |
| BA32 | L-Xyloside | not observed | | 4.11 | 8.3 | β only | 674.4273[b] | 674.4274 |
| ABA1 | D-Altroside | not observed | | 4.55 | 4.6 | β only | 705.4686[b] | 705.4685 |
| ABA2 | D-Fucoside | 4.51 | 4.7 | 4.14 | 8.7 | 1:2 | 689.4747[b] | 698.4735 |
| ABA3 | D-Glucuronide | not observed | | 4.53 | 7.6 | β only | 719.4477[b] | 719.4477 |
| ABA4 | L-Riboside | 4.61 | 4.4 | 4.35 | 9.0 | 1:2 | 675.4594[b] | 675.4579 |
| ABA5 | D-Xyloside | not observed | | 4.11 | 8.7 | β only | 673.4435[b] | 673.4433 |

[a] Most-active Neoglycosides in gray.
[b] HRMS (ESI) m/z for [m + Na].
[c] Anomeric proton obscured by another peak.
[d] Not determined.
[e] HRMS (ESI) m/z for [M − H].
[f] Single anomeric proton signal detected but obscured by another peak.
[g] HRMS (ESI) m/z for [M + H].

Figure 6:
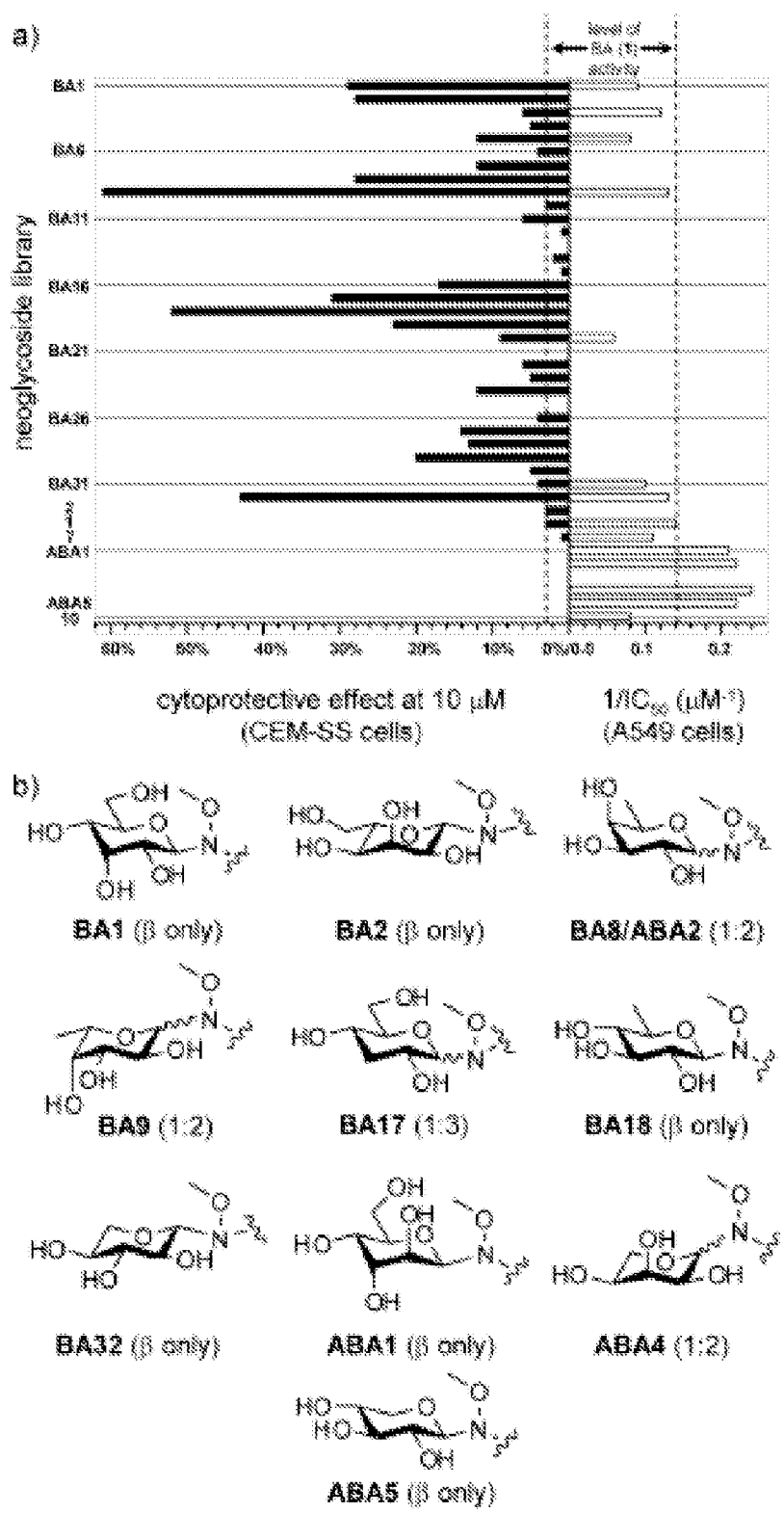
FIG. 6. (a) Divergent activity of betulinic acid neoglycosides against HIV-1-infected CEM-SS cells and A549 cancer cells compared to that of parent 1. (b) Structures of most-active neoglycosides and their anomeric ratios (R$\alpha$:$\beta$).

Two standards, 1 (the parent natural product) and 2 (betulin) were also examined. Eleven library members displayed 1050 values below a threshold of 25 μM (~2-3-fold the activity of 1) in at least one cell line, four of which (D-alloside BA1, D-altroside BA3, L-fucoside BA9, and L-xyloside BA32) were equipotent to the parent in one or more cell lines (FIG. 6 and Table 3).

TABLE 3

IC50 Cytotoxicity Data of BA Neoglycoside Library

| entry | neoglycoside | A549 lung | Du145 prostate | MCF7 breast | SKOV3 Ovary | NC1 H460 Lung | NC1-ADR RES Breast | HT-29 colorectal | HCT15 colorectal | SF-268 Glioblastoma |
|---|---|---|---|---|---|---|---|---|---|---|
| BA1 | D-Alloside | 11.2 = 0.7 | 13.7 = 0.6 | 9.2 = 0.6 | n/d[d] | 11.4 = 0.5 | 12 = 1 | 17.6 = 0.8 | — | 24.7 = 0.8 |
| BA2 | L-Alloside | >25 | >25 | >25 | n/d | >25 | >25 | — | — | — |
| BA3 | D-Altroside | 8.4 = 0.4 | 9.0 = 0.3 | 8.6 = 0.2 | n/d | 10.1 = 0.4 | 7.6 = 0.2 | 11.1 = 0.4 | — | 17.6 = 0.6 |
| BA4 | L-Altroside | >25 | >25 | >25 | n/d | >25 | >25 | — | — | — |
| BA5 | D-Arabinoside | 13.2 = 0.6 | 13.9 = 0.5 | 15.9 = 0.4 | n/d | 14.4 = 0.5 | 21.1 = 0.8 | 14.1 = 0.4 | — | 20.4 = 0.6 |
| BA6 | L-Arabinoside | >25 | >25 | >25 | n/d | >25 | >25 | — | — | — |
| BA7 | D-Digitoxoside | >25 | >25 | >25 | n/d | >25 | >25 | — | — | — |
| BA8 | D-Fucoside | >25 | >25 | >25 | n/d | >25 | >25 | — | — | — |
| BA9 | L-Fucoside | 7.8 = 0.5 | 23 = 4 | 21 = 1 | n/d | >25 | >25 | >25 | — | >25 |
| BA10 | D-Galactoside | >25 | 21 = 1 | >25 | n/d | >25 | >25 | 22 = 1 | — | >25 |
| BA11 | L-Galactoside | n/d | >25 | >25 | n/d | >25 | >25 | — | — | — |
| BA12 | D-Galacturonide | n/d | >25 | >25 | n/d | >25 | >25 | — | — | — |
| BA13 | D-GalNAc | n/d | >25 | >25 | n/d | >25 | >25 | — | — | — |
| BA14 | D-Glucoside | n/d | >25 | >25 | n/d | >25 | >25 | — | — | — |
| BA15 | L-Glucoside | >25 | >25 | >25 | n/d | 12 = 1 | 11 = 2 | 22 = 3 | — | n/d |
| BA16 | D-Glucoside, 2-fluoro | n/d | >25 | >25 | n/d | >25 | >25 | — | — | — |
| BA17 | D-Glucoside, 3-deoxy | n/d | >25 | >25 | n/d | >25 | >25 | — | — | — |
| BA18 | D-Glucoside, 6-deoxy | >25 | >25 | 18 = 1 | n/d | >25 | >25 | 18 = 1 | — | >25 |
| BA19 | D-Glucoside, 3-O—Me | n/d | >25 | >25 | n/d | >25 | >25 | — | — | — |
| BA20 | D-Glucuronide | 15.7 = 0.9 | 19 = 1 | 23 = 1 | n/d | 19.8 = 0.6 | 20 = 2 | 18.8 = 0.4 | — | 23.7 = 0.2 |
| BA21 | D-Glucurono-lactonide | >25 | >25 | >25 | n/d | >25 | >25 | — | — | — |
| BA22 | D-Lyxoside | >25 | >25 | >25 | n/d | >25 | >25 | — | — | — |
| BA23 | L-Lyxoside | >25 | >25 | >25 | n/d | >25 | >25 | — | — | — |
| BA24 | D-Mannoside | >25 | >25 | >25 | n/d | >25 | >25 | — | — | — |
| BA25 | L-Mannoside | >25 | 13 = 2 | 18 = 0.6 | n/d | 19.1 = 0.6 | 22 = 1 | >25 | — | n/d |
| BA26 | D-ManNAc | >25 | >25 | >25 | n/d | >25 | >25 | — | — | — |
| BA27 | L-Rhamnoside | >25 | >25 | >25 | n/d | >25 | >25 | — | — | — |
| BA28 | D-Riboside | >25 | >25 | >25 | n/d | >25 | >25 | — | — | — |
| BA29 | L-Riboside | >25 | >25 | >25 | n/d | >25 | >25 | — | — | — |
| BA30 | D-Taloside | >25 | >25 | >25 | n/d | >25 | >25 | — | — | — |
| BA31 | D-Xyloside | 10.5 = 0.5 | 11 = 2 | 11.8 = 0.4 | >25 | 11.8 = 0.3 | 20.1 = 0.4 | 13.8 = 0.6 | — | 18.7 = 0.3 |
| BA32 | L-Xyloside | 7.5 = 0.3 | 7.0 = 0.2 | 9.0 = 0.3 | >25 | 8.4 = 0.3 | 13.3 = 0.4 | 8.8 = 0.3 | — | 11.8 = 0.2 |
| 2 | Botulin | >25 | >25 | >25 | >25 | >25 | >25 | — | — | — |
| 1 | Botulinic acid | 7.3 = 0.3 | 10.4 = 0.2 | 8.2 = 0.3 | >25 | 7.8 = 0.6 | 7.5 = 0.3 | 12.7 = 0.3 | — | 10.7 = 0.4 |

TABLE 3-continued

IC50 Cytotoxicity Data of BA Neoglycoside Library

| 7 | BA aglycon | 9.5 = 0.2 | 10.1 = 0.4 | 8.7 = 0.5 | 20 = 4 | 16.1 = 0.6 | 22 = 1 | 6.3 = 0.5 | — | 15.3 = 5 |
|---|---|---|---|---|---|---|---|---|---|---|
| ABA1 | D-Altroside | 4.8 = 0.4 | 7.1 = 0.3 | 4.7 = 0.2 | — | — | — | >25 | 12.1 = 0.5 | — |
| ABA2 | D-Fucoside | 4.5 = 0.4 | 5.3 = 0.2 | 4.1 = 0.2 | — | — | — | >25 | 9.9 = 0.4 | — |
| ABA3 | D-Glucuronide | >25 | >25 | >25 | — | — | — | >25 | >25 | — |
| ABA4 | L-Riboside | 4.2 = 0.4 | 6.1 = 0.4 | 3.7 = 0.2 | — | — | — | >25 | 10.0 = 0.4 | — |
| ABA5 | D-Xyloside | 4.6 = 0.5 | 7.2 = 0.9 | 6 = 1 | — | — | — | >25 | 11.0 = 0.4 | — |
| 10 | ABA aglycon | 12 = 1 | 10.3 = 0.9 | 8.2 = 0.7 | — | — | — | >25 | 21 = 1 | — |

[a]Libraries and controls were found to be inactive against MDA-MB-231 breast cancer cell line.
[b]Most-active Neoglycosides in gray.
[c]All values in μM.
[d]No activity detected.

Figure 7:
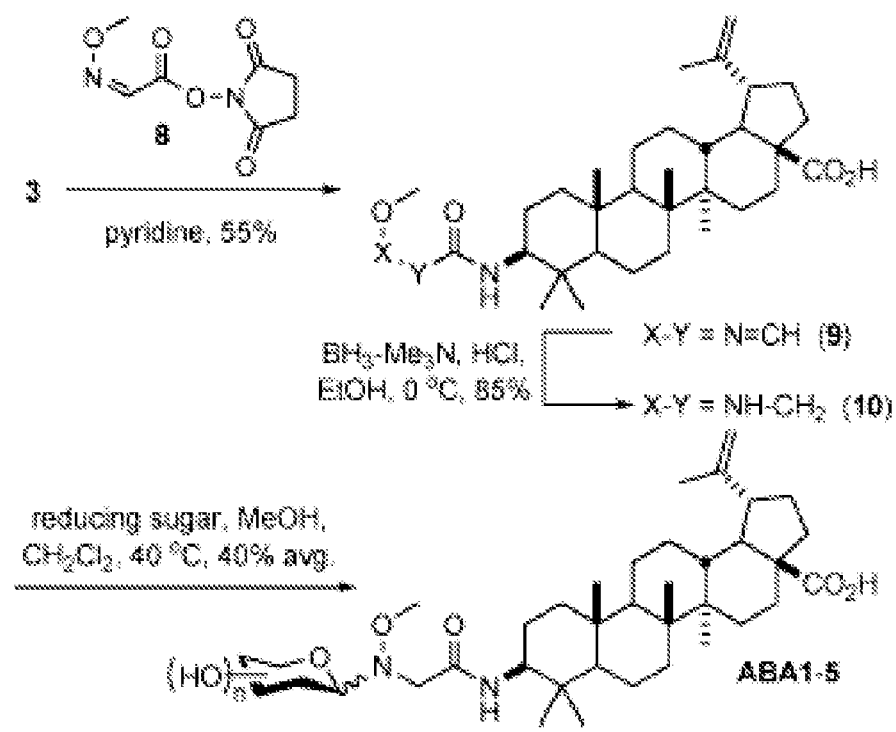
FIG. 7. Scheme 3—the synthesis of 3-aminobetulinic acid neoglycosides.
Figure 8A:
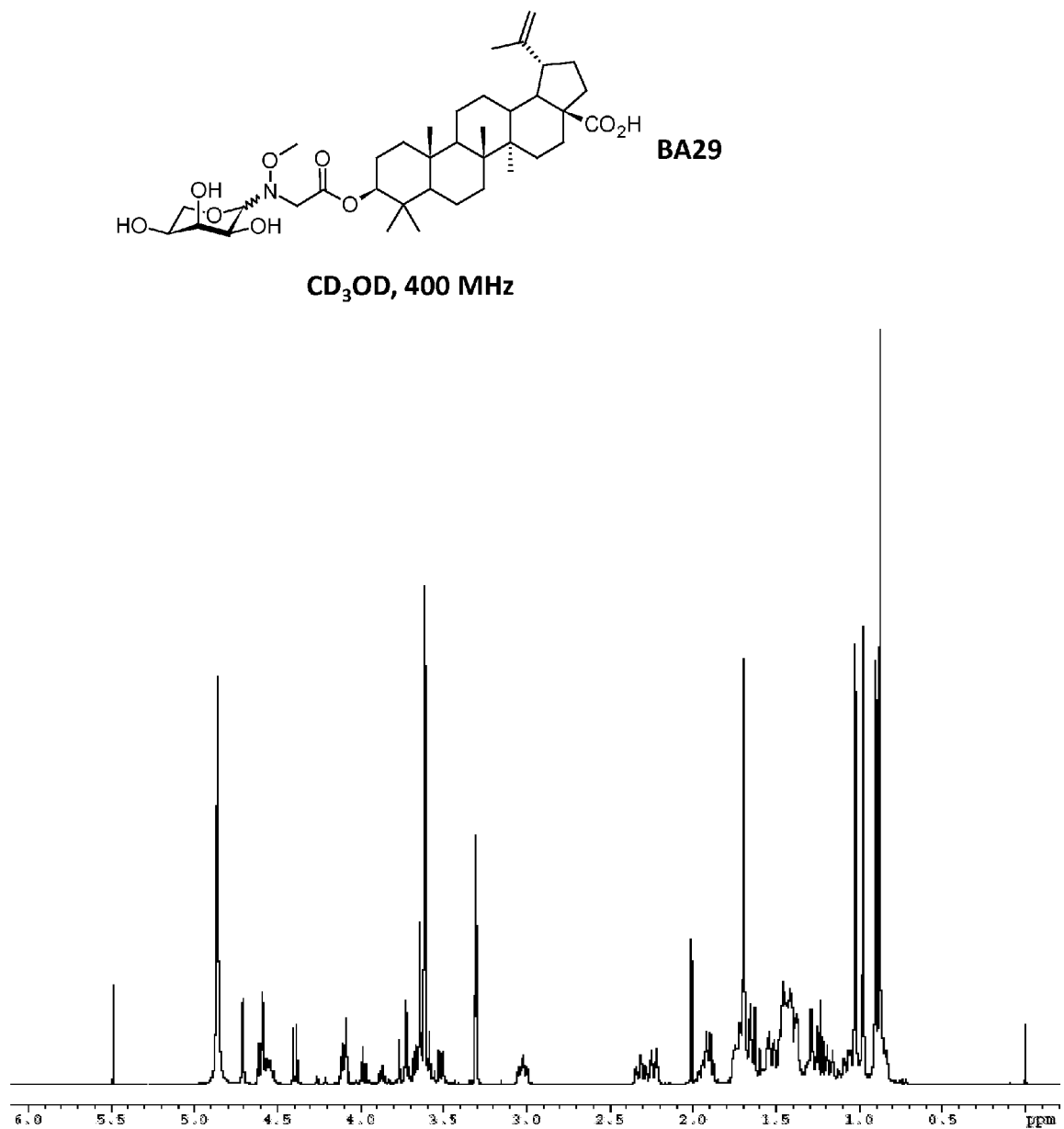
FIG. 8. (a-d) NMR and column chromatography data for BA29.
Figure 8B:
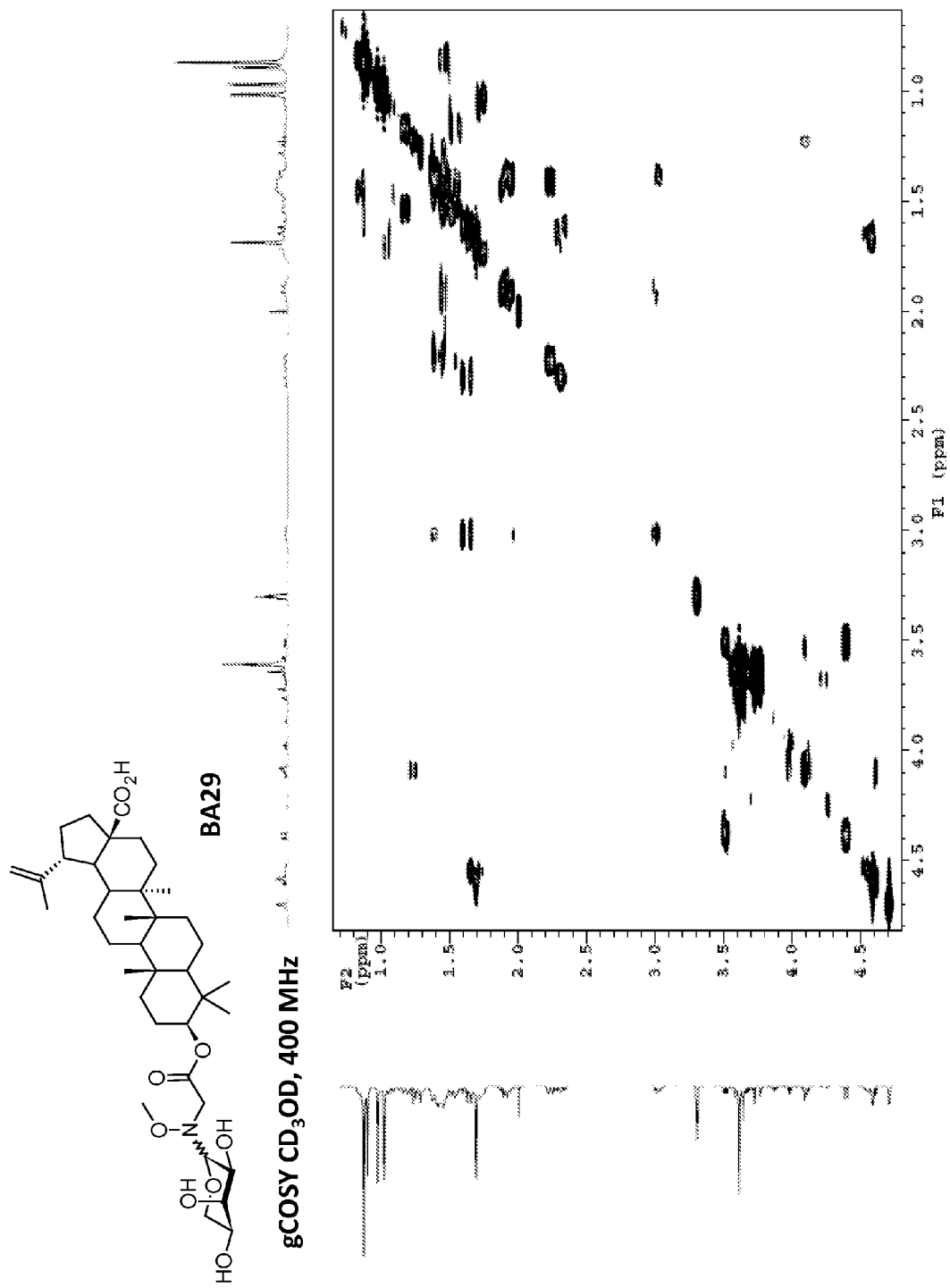
Figure 8C:
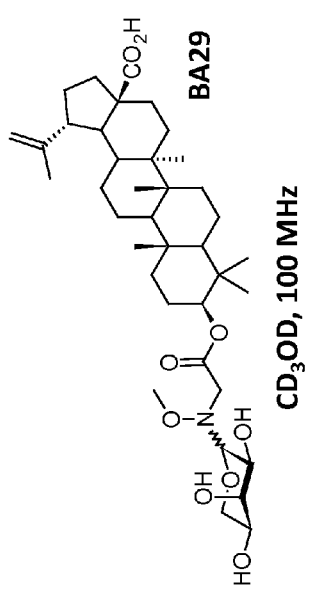
Figure 8C:
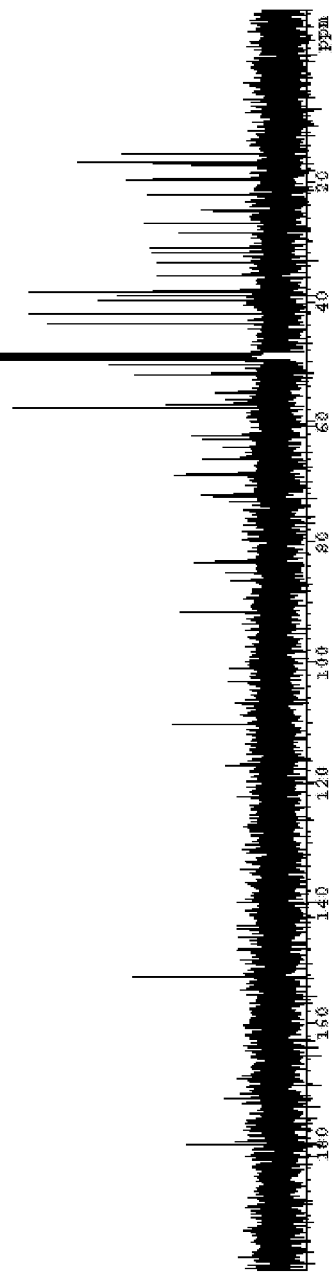
Figure 8D:
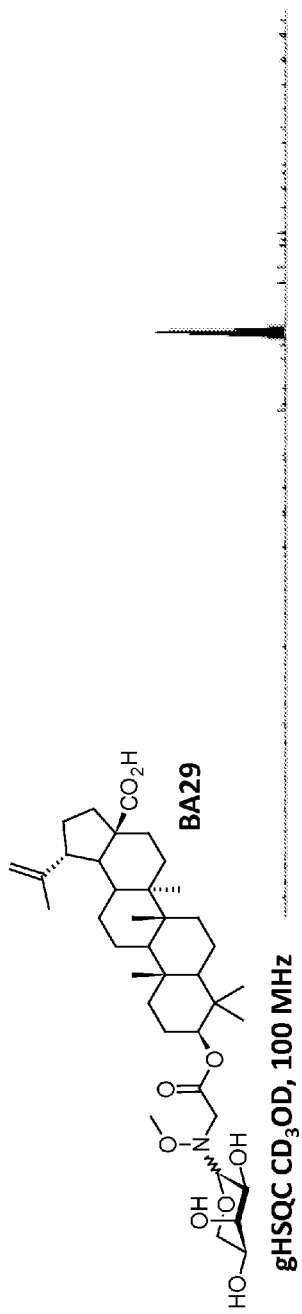
Figure 8D:
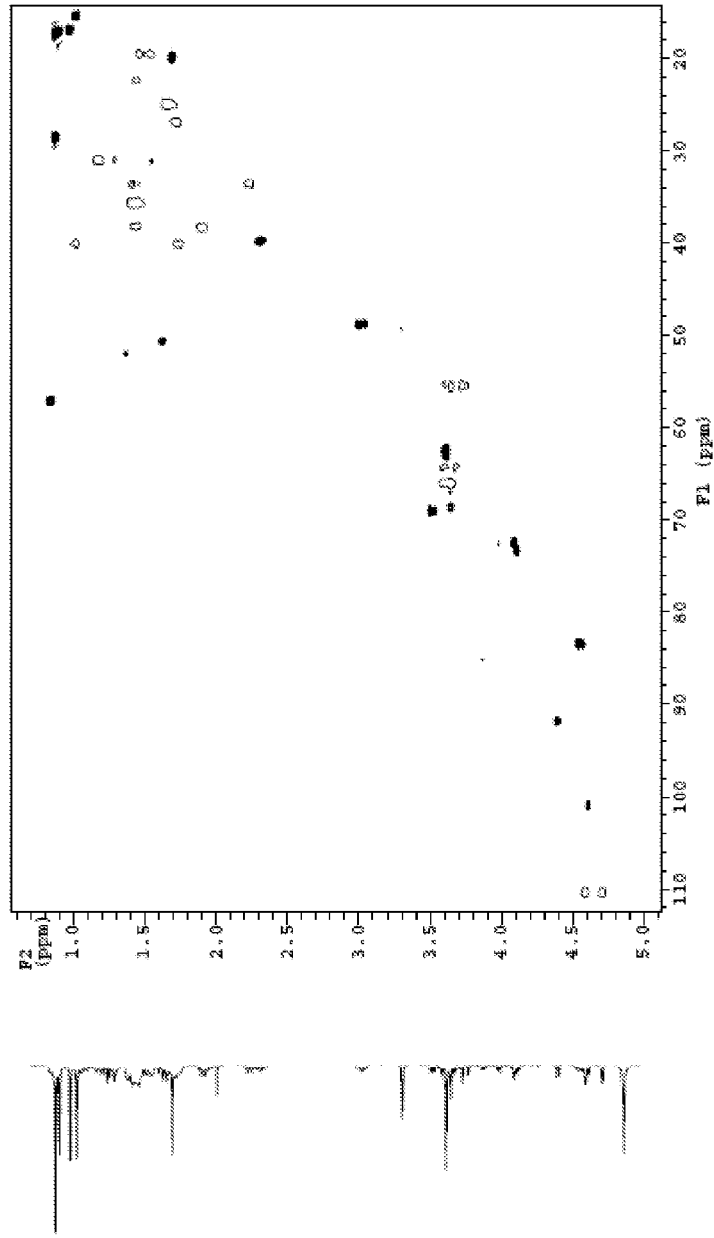
Figure 9A:
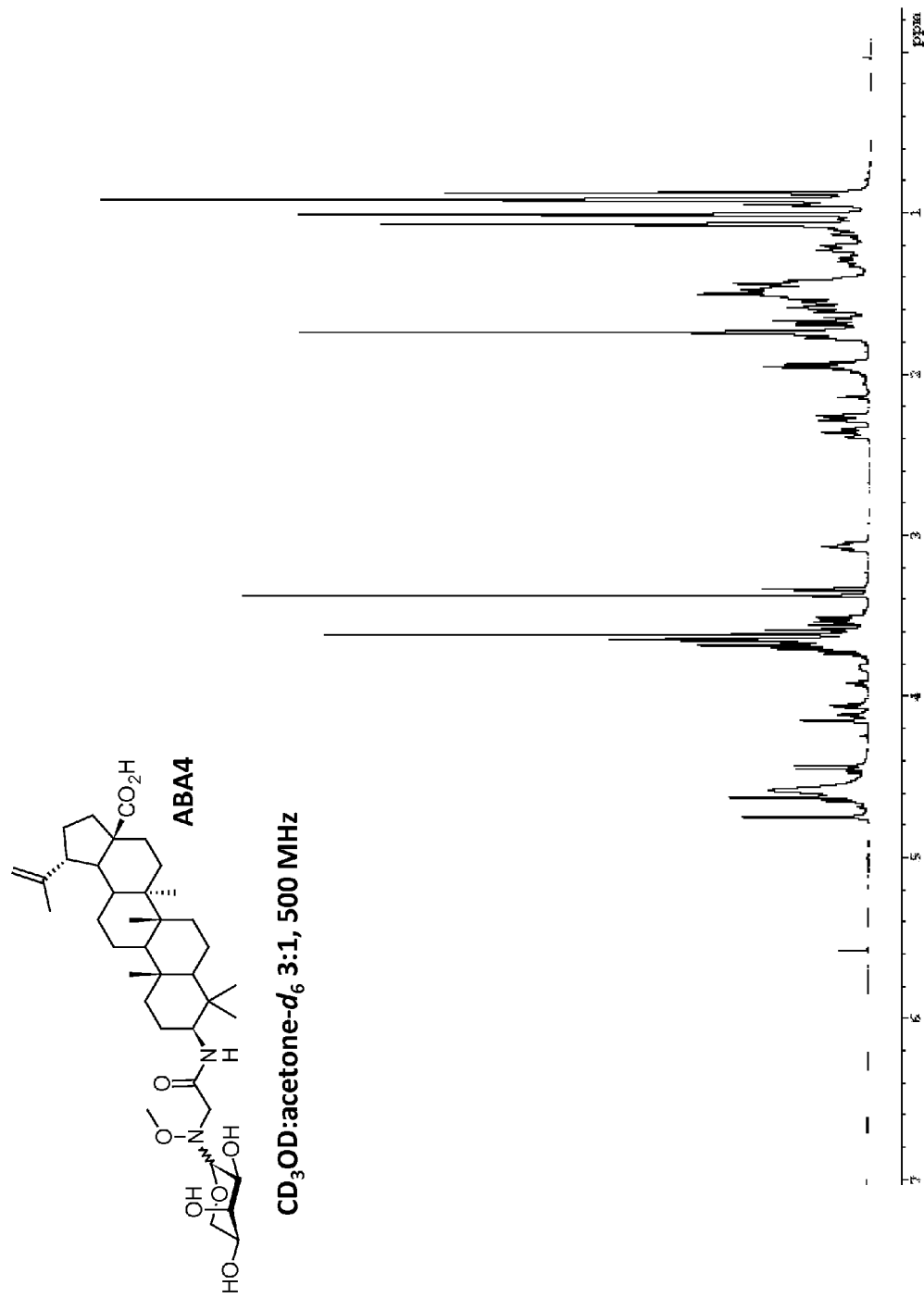
FIG. 9. (a-d) NMR and column chromatography data for ABA4.
Figure 9B:
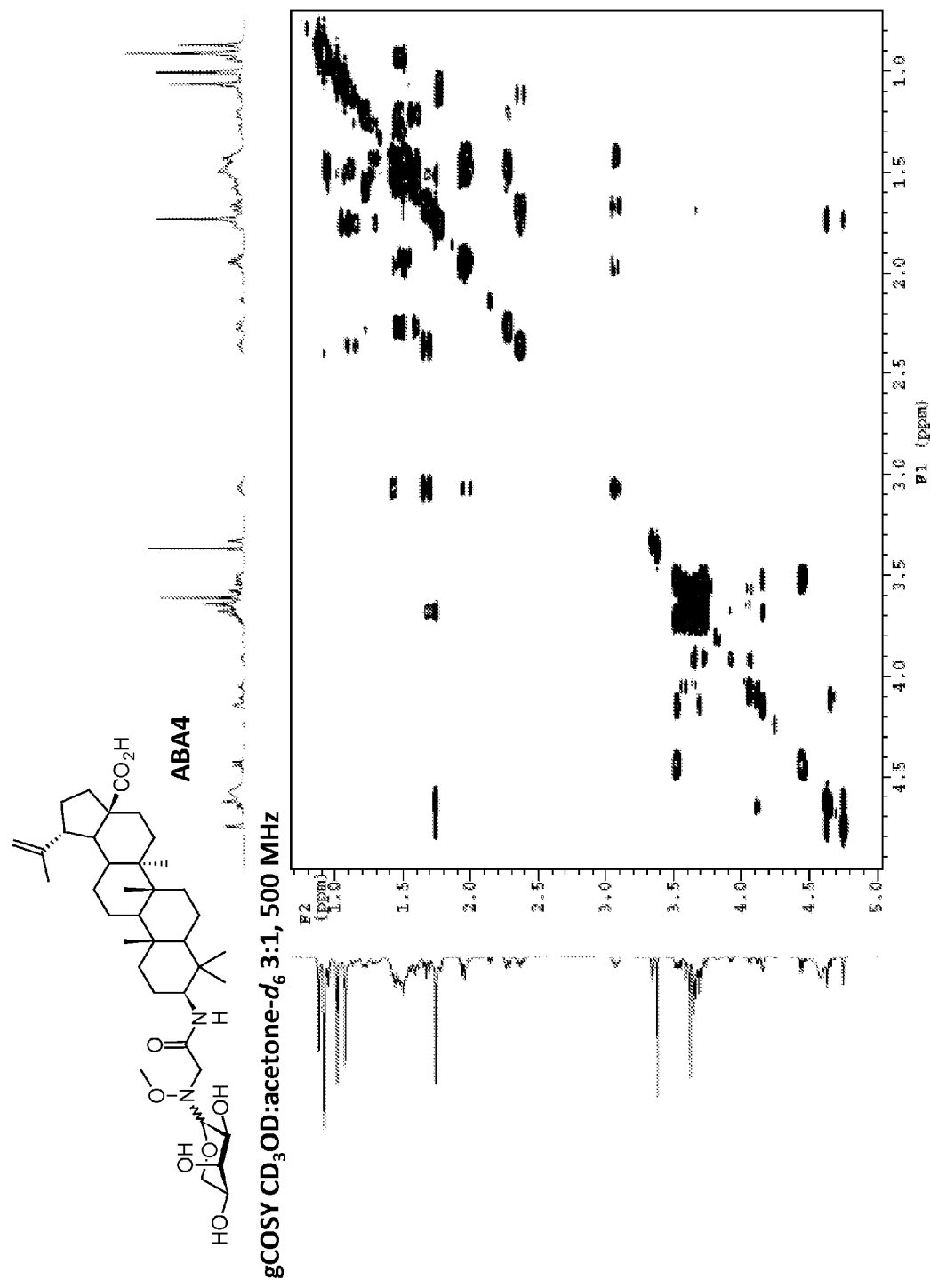
Figure 9C:
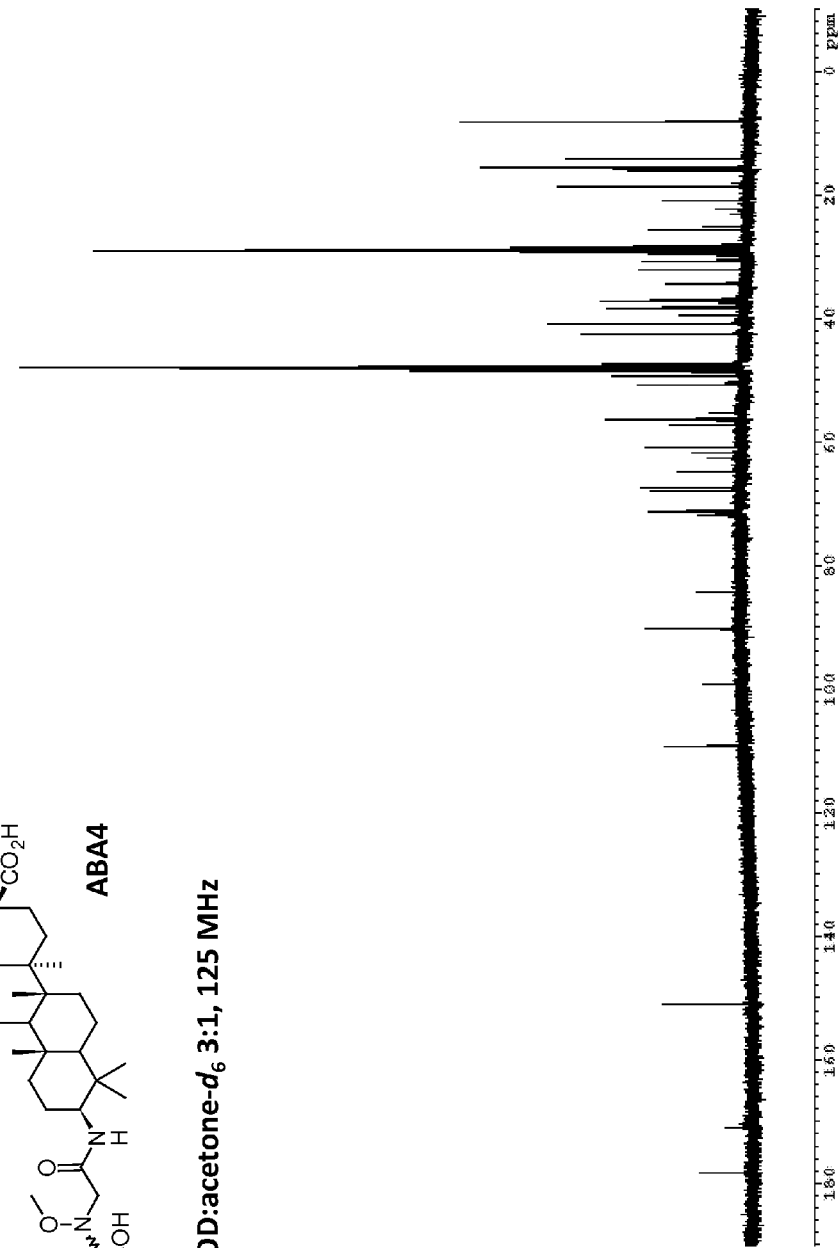
Figure 9D:
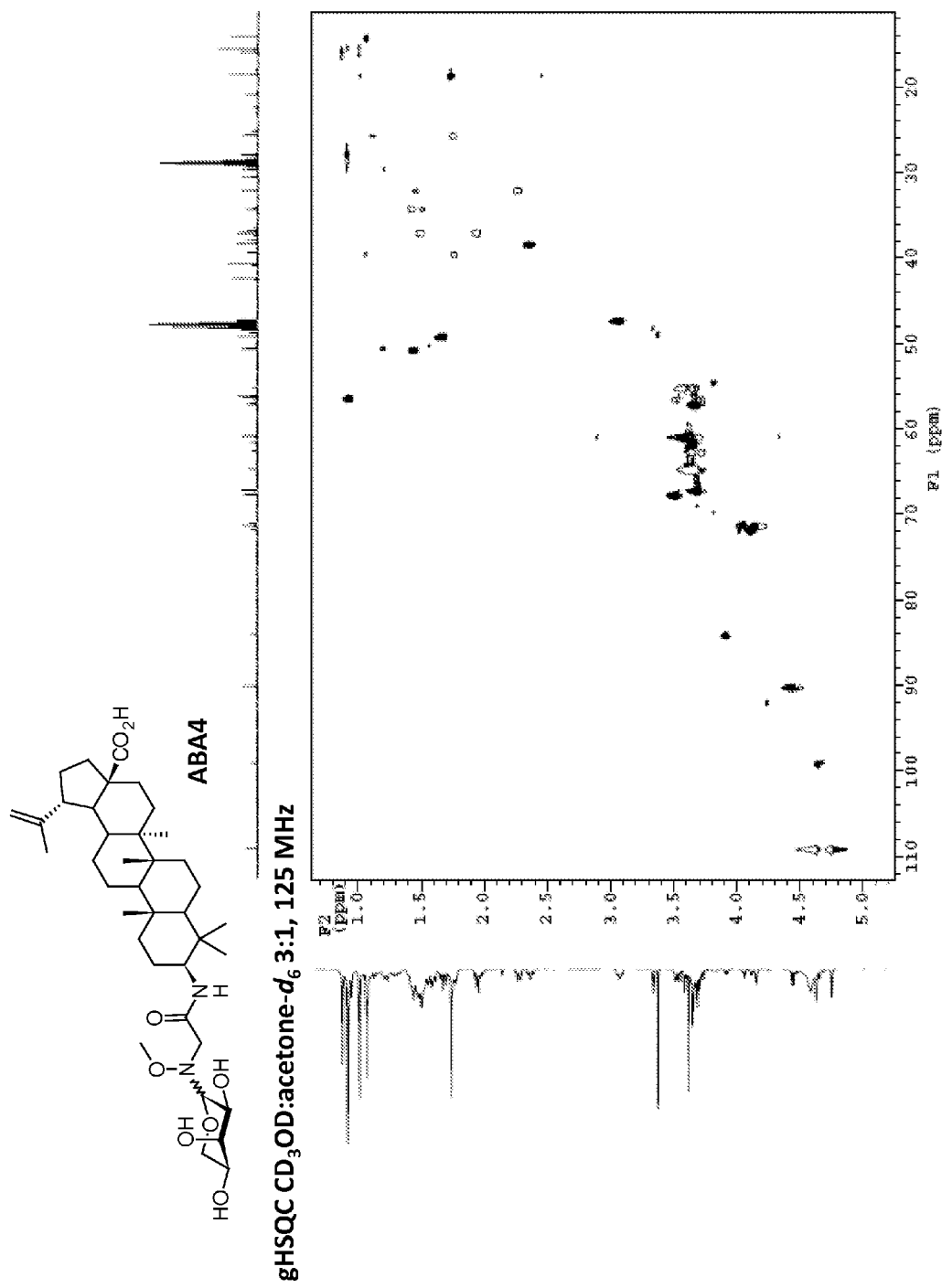

To assess the impact of the ester linker on this activity, a subset of representative amide-linked neoglycosides was subsequently synthesized. This group was designed to represent diverse sugar structures and a range of potencies (as defined by the ester-linked series)—specifically, one equipotent hexose (D-altrose), a 'lower threshold' (IC50~10-20 μM) pentose (D-xylose), an 'upper threshold' (IC50~15-25 μM) hexosuronic acid (D-glucuronate), and a representative threshold (IC50≥25 μM) pentose (L-ribose) and deoxyhexose (D-fucose). To circumvent the need for BA C28 acid protection during C3 acylation, handle installation was accomplished via a standard amidation/reductive amination process. Specifically, N-hydroxysuccinimidyl ester 8 was reacted with 3 in pyridine (FIG. 7) and the resulting imine (9) was reduced with BH3.Et3N complex in the presence of ethanolic HCl to provide aglycon 10 in good yield (85%).

Neoglycosylation of 10 was performed as described above for ester 7, employing identical conditions to produce ABA1-5 (FIG. 5) with an average isolated yield of 33%. These five compounds had a notably decreased bias toward the β-anomer and expectantly displayed the same anomeric ratios as their ester analogs (see Table 2).

The cytoxicity of ABA1-5 was evaluated in human cell lines of breast, colorectal, lung and prostate carcinomas. Interestingly, although aglycons 7 and 10 displayed relatively similar potencies to parent 1, the activities of four (D-altroside ABA1, D-fucoside ABA2, L-riboside ABA4, and D-xyloside ABA5) of the five glycosylated ABA subset were slightly improved over the parent natural product (~2-fold). A comparison of the ester-linked and amide-linked series also revealed clear improvements (2- to ≥5-fold) with these same four sugars in the ABA group (FIG. 7 and Table 3).

While it is tempting to attribute this amide-versus-ester trend simply to the potential stability differences of the neoglycosylation linkers, the differences in magnitude of potency improvement (e.g., ≤2-fold for D-xylosides BA31 versus ABA5 compared to ≥6-fold for L-ribosides BA29 versus ABA4) or cell line selectivity (e.g., a reversal in potency trend between amide series ABA1/ABA3/ABA5 and ester series BA3/BA20/BA31 in HT-29) may contradict this straightforward explanation.

It is also important to note that there appears to be no correlation between the current study and the previous Pichette O-glycoside study. For example, the best sugar in the context of direct C3-Oglycosylation, L-rhamnose, was inactive in the context of an ester-linked neoglycoside (BA27, ≥25 μM). In a similar manner, one of the best sugars in the context of either neoglycosylation approach, D-xylose (BA31 and ABA5), led to a slight decrease in potency as the C3-O-glycoside.

To assess the corresponding impact of differential glycosylation upon antiviral activity, the entire set of compounds was subsequently tested in a single dose (10 μM) anti-HIV-1 assay against CEM-SS cells (i.e., CD4+ T lymphocytes) infected with the IIIB strain of HIV-1. Compound efficacy was determined by the percent increase of cytoprotective effect (CPE), which is prevention of intercellular virus replication, over untreated HIV-1-infected cells.

Under these conditions, 19 of 32 ester-linked compounds displayed at least a 2-fold improvement over parent 1 with seven (D-alloside BA1, L-alloside BA2, D-fucoside BAB, L-fucoside BA9, 3-BA17, 6-deoxy-D-glucoside BA18 and L-xyloside BA32) displaying ≥10-fold enhancements (the most active being ~20-fold better than parent 1, see FIG. 7 and Table 4).

TABLE 4

| CEM-SS Cytoprotection Data for BA Neoglycoside Library | | | |
|---|---|---|---|
| Entry | Neoglycoside | % increase in CPE | % Cell viability |
| BA1 | D-Alloside | 29 | 100 |
| BA2 | L-Alloside | 28 | 100 |
| BA3 | D-Altroside | 6 | 99 |
| BA4 | L-Altroside | 5 | 98 |
| BA5 | D-Arabinoside | 12 | 100 |
| BA6 | L-Arabinoside | 4 | 99 |
| BA7 | D-Digitoxoside | 12 | 100 |
| BA8 | D-Fucoside | 28 | 100 |
| BA9 | L-Fucoside | 61 | 92 |
| BA10 | D-Galactoside | 3 | 100 |
| BA11 | L-Galactoside | 6 | 100 |
| BA12 | D-Galacturonide | 1 | 100 |
| BA13 | D-GalNAc | n/d[d] | 100 |
| BA14 | D-Glucoside | 2 | 97 |

TABLE 4-continued

| CEM-SS Cytoprotection Data for BA Neoglycoside Library | | | |
|---|---|---|---|
| BA15 | L-Glucoside | 1 | 78 |
| BA16 | D-Glucoside, 2-fluoro | 17 | 98 |
| BA17 | D-Glucoside, 3-deoxy | 31 | 99 |
| BA18 | D-Glucoside, 6-deoxy | 52 | 94 |
| BA19 | D-Glucoside, 3-O—Me | 23 | 92 |
| BA20 | D-Glucuronide | 9 | 100 |
| BA21 | D-Glucuronolactonide | n/d | 91 |
| BA22 | D-Lyxoside | 6 | 90 |
| BA23 | L-Lyxoside | 5 | 88 |
| BA24 | D-Mannoside | 12 | 89 |
| BA25 | L-Mannoside | n/d | 33 |
| BA26 | D-ManNAc | 4 | 100 |
| BA27 | L-Rhamnoside | 14 | 100 |
| BA28 | D-Riboside | 13 | 100 |
| BA29 | L-Riboside | 20 | 100 |
| BA30 | D-Taloside | 5 | 99 |
| BA31 | D-Xyloside | 4 | 100 |
| BA32 | L-Xyloside | 43 | 99 |
| 2 | Botulin | 3 | 92 |
| 1 | Botulinic acid | 3 | 100 |
| 7 | BA aglycon | 1 | 100 |
| ABA1 | D-Altroside | n/d (n/d) | 59 (100) |
| ABA2 | D-Fucoside | n/d (12) | 9 (100) |
| ABA3 | D-Glucuronide | n/d (32) | 24 (100) |
| ABA4 | L-Riboside | n/d (7) | 97 (100) |
| ABA5 | D-Xyloside | n/d (4) | 52 (100) |
| 10 | 3-Aminobec, acid aglycon | n/d (n/d) | 73 (100) |
| — | AZT | 18 | 100 |
| — | Indinavir | 32 | 100 |

[a]Most active Neoglycoside in gray.
[b]Cytoprotective effect.
[c]CPE at 10 μM unless otherwise indicated.
[d]No activity detected.
[e]CPE at 1 μM.
[f]Cell viability at 1 μM.
[g]CPE at 10 μM.

It is important to note that at 10 μM, host cell cytotoxicity of the ester series was not a contributing factor as only 4 of the 32 esters led to ≥10% reduction of host cell viability. In contrast, antiviral activity could not be achieved without significant host cell cytotoxicity with amides ABA1-5 or aglycon 10.

Dilution of the amide series to 1 μM abated host cell cytotoxicity, yet only D-glucuronide ABA3 demonstrated any significant CPE (32% increase in CPE), while 10 had no noticeable activity at 1 μM (see Table 4).

III. EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Materials and General Methods

Mass spectrometric data were obtained on either a Waters AutoSpec (Beverly, Mass.) spectrometer for electron ionization (EI; 70 eV) or a Waters LCT time of-flight spectrometer for electrospray ionization (ESI). NMR spectra were obtained on a Varian Unitylnova 400 or 500 MHz instrument (Palo Alto, Calif.) using 99.8% $CDCl_3$ with 0.05% v/v TMS or 99.8% CD3OD, 99.9% acetone-d6, or 99.5% pyridine-d5 in ampoules. 1H and 13C chemical shifts were referenced to nondeuterated solvent or TMS (where included). Multiplicities are indicated by s (singlet), d (doublet), t (triplet), q (quartet), m (multiplet), and br (broad). Chemical shift assignments for anomeric mixtures, where possible, are noted as α or β with the atom responsible for the shift.

1H NMR characterization was supplemented with gCOSY for all neoglycoside library members as well as 13C and gHSQC for pilot reactions. Tetrahydrofuran was dried using a column of activated alumina. All other solvents were used as provided.[20] Reagents were obtained from Aldrich or Sigma and were used as received. Flash chromatography was performed using 40-63 μm particle sized silica gel. Thin layer chromatography was performed on aluminum-backed, 254 nm UV-active plates with a silica gel particle size of 60 μm.

General procedure for neoglycoside library synthesis and purification. Aglycons 7 or 10 (typically 0.053-0.064 mmol) were added to 1 dram vials along with stir fleas and dissolved in $CH_2Cl_2$ (100 μL). The volumes were adjusted with MeOH (~600 μL) to provide the aglycon at a concentration of 90-100 mM. Reducing sugars (3 eq.) were added, the vials capped, and the vessels placed on a heating block/stir plate to react for 48 h at 40° C. The vial caps were removed and the solvent evaporated by a Speedvac apparatus (55° C., 3 h).

Crude neoglycosides were suspended in MeOH:$CH_2Cl_2$ 5:95 (250 μL) with sonication (5 min) and then purified via 2000 mg silica gel solid phase extraction (SPE) columns (Alltech, Deerfield, Ill.) prewashed with MeOH:CH2Cl2 5:95. The SPEs were eluted using a vacuum manifold, collecting fractions with a volume of approximately 1.5 mL. After the initial two fractions were obtained, eluting any unreacted aglycon, the isocratic separation was continued for pentoses and substituted hexoses while a step gradient of MeOH:CHCl3 15:85 was used for hexoses or MeOH:CHCl3 20:80 for glycuronosides.

Typically, all neoglycoside was eluted by the seventh or eighth fraction leaving unreacted sugar on the SPE column. The fractions containing pure product were identified by TLC using p-anisaldehyde stain, then combined and dried. Compounds were assayed by 1H and gCOSY NMR as well as high-resolution Electrospray ionization mass spectrometry. Anomeric ratios were obtained by comparison of anomeric proton integration (see Table 2).

Example 2

Synthesis of (3S)-N-Methoxyaminobetulinic acid (5)

3-N-Methoxyiminobetulinic acid (4, 660 mg, 1.36 mmol), which was prepared as described, S1 was dissolved in a 1:2 solution of MeOH:p-dioxane (9 mL) and cooled to 0° C. The reducing agent BH3.tBuNH2 was added followed by dropwise addition of 10% aqueous HCl (4 mL) over 5 m. After 1 h, the reaction was quenched with solid $Na_2CO_3$ (150 mg) and allowed to warm to room temperature. $CH_2Cl_2$ (30 mL) was added and the reaction mixture was washed with saturated aqueous $NaHCO_3$ (5 mL) and dried over $Na_2SO_4$. After solvent removal, the diastereomers were separated by column chromatography (SiO2, EtOAc:Hex 1:5), yielding both as white solids (3S: 300 mg, 45%, Rf=0.39 EtOAc:Hex 1:4; 3R: 114 mg, 17%, Rf=0.47 EtOAc:Hex 1:4). 1H NMR ($CDCl_3$, 400 MHz) δ 4.74 (d, J=1.6 Hz, 1 H), 4.62 (s, 1 H), 3.51 (s, 3 H), 3.01 (td, J=10.7, 4.7 Hz, 1 H), 2.47 (dd, J=11.7, 4.1 Hz, 1 H), 2.27 (dt, J=12.6, 3.1 Hz, 1 H), 2.19 (td, J=12.6, 3.5 Hz, 1 H), 2.04-1.85 (m, 2 H), 1.74-1.58 (m, 7 H), 1.55-1.32 (m, 6 H), 1.31-1.14 (m, 9 H), 1.11-1.04 (m, 2 H), 0.98 (s, 3 H), 0.93 (s, 3 H), 0.90-0.84 (m, 1 H), 0.82 (s, 3 H), 0.76-0.70 (m, 1 H), 0.67 (s, 3 H); $^{13}C$ NMR ($CDCl_3$, 100 MHz) δ 182.56, 150.65, 109.89, 68.30, 61.86, 56.90, 56.64, 50.75, 49.49, 47.16, 42.64, 40.90, 38.90, 38.66, 37.50, 37.30, 36.92, 34.52, 32.41, 30.81, 29.91, 28.70, 25.73, 23.79, 20.99, 19.59, 18.31, 16.70, 16.29, 16.12, 14.91; HRMS (ESI) m/z for C31H50NO3 ([M−H]−) 484.3792, calc. 484.3791.

Example 3

Synthesis of (3S)-O-Chloroacetylbetulinic acid (6)

Betulinic acid (1, 335 mg, 0.734 mmol) and DMAP (9 mg, 0.07 mmol) were dissolved in anhydrous THF (20 mL) under Ar. Diisopropylethylamine (190 μL, 1.09 mmol) was added followed by dropwise addition of chloroacetyl chloride (120 μL, 1.51 mmol), soon after which the reaction became cloudy. After stirring for 2 h, absolute ethanol (500 μL) was used to quench the reaction. The solvent was removed in vacuum and the resulting crude solid was adsorbed onto silica gel, after dissolving in $CH_2Cl_2$ (5 mL), then purified by column chromatography (SiO2, EtOAc:Hex 1:5) to give the desired chloroacetate as a white solid (338 mg, 86%, Rf=0.57 EtOAc:Hex 1:4). 1H NMR ($CDCl_3$, 400 MHz) δ 4.74 (d, J=1.9 Hz, 1 H), 4.62 (t, J=1.3 Hz, 1 H), 4.57 (m, 1 H), 4.05 (d, J=2.4 Hz, 2 H), 3.01 (td, J=10.9, 4.7 Hz, 1 H), 2.28 (dt, J=12.5, 3.1, 1 H), 2.19 (td, J=12.6, 3.3 Hz, 1 H), 2.03-1.94 (m, 2 H), 1.74-1.58 (m, 10 H), 1.55-1.47 (m, 3 H), 1.46-1.34 (m, 9 H), 1.33-1.25 (m, 2 H), 1.21-1.16 (m, 1 H), 0.98 (s, 3 H), 0.94 (s, 3 H), 0.87 (s, 3 h), 0.85 (s, 3 H), 0.82-0.78 (m, 1 H); $^{13}C$ NMR ($CDCl_3$, 100 MHz) δ 182.10, 167.36, 150.56, 109.98, 83.58, 56.60, 55.59, 50.60, 49.50, 47.16, 42.66, 41.47, 40.92, 38.62, 38.53, 38.24, 37.33, 34.42, 32.36, 30.77, 29.90, 28.15, 27.14, 25.63, 21.08, 19.56, 18.33, 16.62, 16.39, 16.25, 14.89; HRMS (ESI) m/z for C32H49ClNaO4 ([M+Na]+) 555.3209, calc. 555.3217.

Example 4

Synthesis of (3S)-O-(N-Methoxyglycyl)betulinic acid (7)

Procedure A (<500 mg batches): Chloroacetate 6 (177 mg, 0.333 mmol) was dissolved in absolute ethanol (16 mL) along with NaI (160 mg, 1.07 mmol) under Ar. After stirring at room temperature for 40 min, a solution of MeONH2 in THF (1.7 M, 2 mL, 3.4 mmol; made by mixing MeONH3Cl in a NaOH/THF slurry for 16 h) was added, the inert gas line removed, and the reaction heated to 60° C. After 14 h, and again at 16 h, another equivalent of MeONH2 reagent was added. At 19 h total, the solvent was removed in vacuo and the crude solid was purified by column chromatography (SiO2, EtOAc:Hex 1:3) to give the desired aglycon as a white sticky solid (120 mg, 67%, Rf=0.26 EtOAc:Hex 1:3).

Procedure B (≥500 mg batches): Chloroacetate 4 (1.20 g, 2.25 mmol) was dissolved in absolute ethanol (100 mL) along with NaI (1.01 g, 6.75 mmol) under Ar. After stirring at room temperature for 2 h, a solution of MeONH2 in THF (2.4 M, 1.9 mL, 4.56 mmol) was added, the inert gas line removed, and the reaction heated to 60° C. Two hours after base addition, the reaction was cooled to room temperature and another aliquot of MeONH2 in THF (2 eq.) was introduced followed by reheating to 60° C. This additive process was repeated roughly every 2 h until the reaction had progressed sufficiently (based upon TLC, EtOAc:Hex 1:3) which occurred after ~24 h of total reaction time. The solvent was removed and the product purified as described above (610 mg, 50%). 1H NMR (CDCl3, 400 MHz) δ 4.71 (s, 1 H), 4.58 (s, 1 H), 4.55 (m, 1 H), 3.60 (d, J=4.4 Hz, 2 H), 3.51 (s, 3 H), 2.98 (td, J=10.5, 4.4 Hz, 1 H), 2.25 (d, J=2.7 Hz, 1 H), 2.16 (td, J=12.5, 3.2 Hz, 1 H), 2.00-1.89 (m, 2 H), 1.72-1.53 (m, 11 H), 1.52-1.45 (m, 2 H), 1.44-1.32 (m, 6 H), 1.25-1.21 (m, 1 H), 1.18-1.12 (m, 1 H), 1.04-0.99 (m, 1 H), 0.95 (s, 3 H), 0.91 (s, 3 H), 0.83 (s, 6 H), 0.81 (s, 3 H), 0.80-0.75 (m, 1 H); $^{13}C$ NMR ($CDCl_3$, 100 MHz) δ 181.31, 170.97, 150.50, 109.78, 82.17, 61.52, 56.43, 55.47, 53.14, 50.48, 49.32, 46.99, 42.50, 40.78, 38.43, 37.96, 37.18, 37.14, 34.30, 32.26, 30.65, 29.78, 27.99, 25.52, 23.80, 20.95, 19.42, 18.23, 16.57, 16.25, 16.05, 14.74; HRMS (ESI) m/z for C33H53NaNO4 ([M+Na]+) 566.3820, calc. 566.3821.

Example 5

Synthesis of (3S)-Aminobetulinic acid (3)

Betulinic acid (650 mg, 1.43 mmol) was dissolved in methanol (25 mL) with strong agitation. Ammonium acetate (1.11 g, 14.4 mmol) and NaCNBH3 (61 mg, 0.97 mmol) were then combined to the reaction vessel. After 8 h, the clear reaction solution turned to a cloudy mixture, which remained until 40 h when the reaction was quenched with conc. HCl to a pH of 2. The methanol was removed in vacuo and the aqueous remainder diluted with 25 mL of deionized water. The mixture was extracted with Et2O (20 mL), resulting in an emulsion that required separation by centrifugation (4000 rpm, 4 m). After removal of the organic layer, the process of Et2O extraction and centrifugation was repeated twice more. The pH of the combined aqueous layer and resulting solid mass was adjusted to 10 with KOH flakes, inducing the appearance of more white precipitate. Further centrifugation separated the desired product as a solid mass, which dried to a fluffy white powder (651 mg, >99%, Rf=0.26 EtOAc:Hex 2:1). 1H NMR (pyridine-d5:acetone-d6 9:1, 400 MHz) δ 4.96 (d, J=1.9 Hz, 1 H), 4.79 (dd, J=2.2, 1.3 Hz, 1 H), 3.54-3.48 (m, 1 H), 3.04 (dd, J=11.7, 4.2 Hz, 1 H), 2.77-2.69 (m, 1 H), 2.64-2.58 (m, 1 H), 2.27-2.21 (m, 2 H), 2.02-1.93 (m, 2 H), 1.92-1.77 (m, 6 H), 1.74-1.68 (m, 1 H), 1.63-1.56 (m, 8 H), 1.32-1.19 (m, 3 H), 1.15 (s, 3 H), 1.13-1.05 (m, 8 H), 0.91 (s, 3 H), 0.90-0.87 (m, 1 H), 0.82 (s, 3 H); 13C NMR (pyridine-d5:acetone-d6 9:1, 100 MHz) δ 179.04, 151.62, 110.07, 69.12, 56.85, 56.57, 51.31, 49.98, 47.97, 43.10, 41.37, 39.59, 38.82, 37.92, 37.79, 35.05, 33.09, 31.42, 30.50, 29.27, 26.36, 25.80, 21.39, 19.65, 18.90, 17.99, 16.80, 16.60, 15.10; HRMS (EI) m/z for C30H49NO4 ([M]+) 455.3750, calc. 455.3763.

Example 6

Synthesis of N'-Succinimidyl-N-methoxyiminoacetate (8)

N-Methoxyiminoacetic acid (1.10 g, 10.7 mmol) was dissolved in 1:1 p-dioxane:CH2Cl2 (10 mL) followed by the addition of Nhydroxysuccinimide (1.35 g, 11.7 mmol). The reaction was cooled to 0° C. then 1,3-diisopropoylcarbodiimide (1.9 mL, 12.2 mmol) was added. After stirring for 30 min, the resulting suspension was cold-filtered and the solvent removed in vacuo. The white residue was dissolved in THF (5 mL) and passed through a silica gel plug with 1:1 EtOAc:Hex. The white solid (1.78 g, 83%, Rf=0.73 EtOAc:Hex 1:1) was used without further purification. 1H NMR (pyridine-d5, 400 MHz) δ 7.95 (s, 1 H), 3.92 (s, 3 H), 2.88 (s, 4 H); 13C NMR (pyridine-d5, 100 MHz) δ 170.32, 158.62, 138.00, 64.53, 26.53; HRMS (ESI) m/z for C7H9N2O5 ([M+H]+) 201.0526, calc. 201.0506.

Example 7

Synthesis of (3S)-N-(N'-Methoxyiminoacetyl)aminobetulinic acid (9)

(3S)-Aminobetulinic acid (3; 208 mg, 0.456 mmol) was dissolved in pyridine (20 mL) followed by addition of activated ester 8 (107 mg, 0.535 mmol). After 1 h, the solvent was removed in vacuo and the crude material was dissolved in a minimal volume of MeOH:CH$_2$Cl$_2$ 1:1 and adsorbed onto silica gel. Subsequent flash chromatography (SiO2, EtOAc: Hex 1:4) gave the desired purified product as a white amorphous solid (135 mg, 55%, Rf=0.27 EtOAc:Hex 1:4). 1H NMR (CDCl3, 400 MHz) δ 7.41 (s, 1 H), 6.41 (d, J=10.3 Hz, 1 H), 4.75 (s, 1 H), 4.61 (s, 1H), 3.96 (s, 3 H), 3.71 (td, J=11.0, 5.4 Hz, 1 H), 3.07-2.99 (m, 1 H), 2.32-2.18 (m, 2 H), 2.04-1.94 (m, 2 H), 1.76-1.66 (m, 5 H), 1.65-1.29 (m, 15 H), 1.22-1.16 (m, 1 H), 1.11-1.05 (m, 1 H), 0.98 (s, 3 H), 0.94 (s, 3 H), 0.88 (s, 3 H), 0.86-0.85 (m, 1 H), 0.83 (s, 3 h), 0.80 (s, 3H); 13C NMR (CDCl3, 100 MHz) δ 181.70, 171.37, 161.44, 150.66, 109.82, 63.11, 60.57, 56.69, 56.17, 50.59, 49.41, 47.12, 42.59, 40.80, 39.25, 38.52, 38.17, 37.23, 34.37, 32.38, 30.77, 29.85, 28.59, 25.60, 22.95, 20.96, 19.49, 18.68, 16.51, 16.24, 16.18, 14.78; HRMS (ESI) m/z for C33H52N2NaO4 ([M+Na]+) 563.3809, calc. 563.3825.

Example 8

Synthesis of (3S)-N-(N'-Methoxyglycyl)aminobetulinic acid (10)

Imine 9 (359 mg, 0.664 mmol) was dissolved in absolute ethanol (40 mL) and cooled to 0° C. BH3.Me3N complex (484 mg, 6.63 mmol) was added in one aliquot and once fully dispersed, a 50% solution of HCl in absolute ethanol (1.11 mL, 6.71 mmol) was added, in dropwise fashion, over the course of five minutes. The reaction was allowed to warm to room temperature, dissolving the suspended material, and a second equal aliquot of ethanolic HCl was likewise added but at room temperature. After five hours, the reaction was quenched with saturated aqueous NaHCO3 (20 mL) and extracted with CH$_2$Cl$_2$ (4×40 mL). The combined organic layers were washed with brine (20 mL) and dried over Na2SO4. Solvent removal yielded the aglycon as a flaky white solid (306 mg, 85%, Rf=0.43 MeOH:CH$_2$Cl$_2$ 5:95), which was used without further purification. 1H NMR (CDCl$_3$, 500 MHz) δ 6.70 (d, J=9.2 Hz, 1 H), 4.74 (s, 1 H), 4.60 (s, 1 H), 3.74-3.66 (m, 1 H), 3.56 (s, 5 H), 3.07-2.98 (m, 1 H), 2.32-2.19 (m, 2 H), 2.06-1.93 (m, 2 H), 1.76-1.65 (m, 5 H), 1.64-1.29 (m, 15 H), 1.20-1.14 (m, 1 H), 1.07-1.00 (m, 1 H), 0.97 (s, 3 H), 0.94 (s, 3 H), 0.88 (s, 3 H), 0.86 (s br, 1 H), 0.83 (s, 3 h), 0.79 (s, 3 H); 13C NMR (CDCl3, 125 MHz) δ 180.98, 169.67, 150.59, 109.68, 61.99, 56.65, 56.50, 56.17, 55.11, 50.61, 49.40, 47.15, 42.61, 40.84, 39.30, 38.52, 37.93, 37.31, 37.29, 34.43, 32.46, 30.82, 29.90, 28.57, 25.68, 22.88, 21.03, 19.54, 18.75, 16.60, 16.31, 16.27, 14.86; HRMS (ESI) m/z for C33H55N2O4 ([M+H]+) 543.4153, calc. 543.4156.

Example 9

Synthesis of (3S)-O-(N-Methoxy-N-L-ribosylglycyl) betulinic acid (BA29)

Pilot reaction. Aglycon 7 (30 mg, 0.055 mmol) was placed into a 1 dram vial, dissolved in CH$_2$Cl$_2$ (100 μL), and the volume adjusted with methanol (600 μL). After adding L-ribose (41 mg, 0.27 mmol), the reaction was capped, warmed to 40° C. and allowed to stir for 2 d. Solvent was subsequently removed in vacuo and the resulting crude solid suspended in 5:95 methanol:CH$_2$Cl$_2$ (250 μL) by sonication. The mixture was purified by column chromatography (SiO$_2$, MeOH: CH$_2$Cl$_2$ 5:95), providing the white solid neoglycoside as a mixture of anomers (18 mg, 49%, Rf=0.23 MeOH:CH2Cl2 5:95). 1H NMR (CD3OD, 400 MHz) δ 4.71 (d, J=1.9 Hz, 1 H), 4.61 (d, J=3.8 Hz, 0.33H, α-H1), 4.59 (s, 1 H), 4.55 (m, 1 H), 4.39 (d, J=8.8 Hz, 0.67H, β-H1), 4.12-4.09 (m, 1.34 H, 2β), 3.98 (t, J=5.6 Hz, 0.33 H, α), 3.87 (td, J=5.6, 3.7 Hz, 0.33H, α), 3.78-3.75 (m, 0.33 H, α), 3.74-3.70 (m, 0.66 H, 2α), 3.69-3.65 (m, 0.67 H, β), 3.65 (s, 2 H), 3.61 (s, 3 H), 3.60-3.57 (m, 0.67 H, β), 3.52 (dd, J=8.8, 2.9 Hz, 0.67 H, β), 3.03 (td, J=10.7, 4.7 Hz, 1 H), 2.31 (td, J=12.6, 3.4 Hz, 1 H), 2.23 (dt, J=12.6, 3.2 Hz, 1 H), 1.99-1.87 (m, 2 H), 1.77-1.59 (m, 10 H), 1.57-1.50 (m, 2 H), 1.49-1.36 (m, 7 H), 1.32-1.27 (m, 1 H), 1.21-1.14 (m, 1 H), 1.08 (dd, J=12.9, 4.4 Hz, 1 H), 1.02 (s, 3 H), 0.98 (s, 3 H), 0.90 (s, 3H), 0.88 (s, 6H), 0.84 (m, 1H); 13C NMR (CD3OD, 100 MHz) δ 180.18, 172.61, 152.12, 110.35, 100.88 (α-C1), 91.67 (β-C1), 85.13 (a), 83.35, 73.36 (a), 72.54 (β), 72.30 (β), 69.01 (β), 68.64 (β), 66.00, 64.16 (a), 62.96 (a), 62.40, 57.63, 56.99, 55.31, 52.03, 50.58, 48.64, 43.77, 42.10, 39.77, 39.14, 38.45, 38.29, 35.63, 33.50, 31.86, 31.00, 28.61, 26.99, 24.86, 22.28, 19.72, 19.44, 17.16, 16.91, 16.79, 15.32; HRMS (ESI) m/z for C38H61NNaO9 ([M+Na]+) 698.4232, calc. 698.4239 (FIG. 8A-D).

Example 10

Synthesis of (3S)-N-(N'-Methoxy-N'-L-ribosylglycyl)betulinic acid (ABA4)

Pilot reaction. Using the same procedure as BA29 but starting with aglycon 10 (46 mg, 0.085 mmol) yielded the anomeric mixture as a white solid (40 mg, 70%, Rf α=0.50 Rf β=0.45 MeOH:CH$_2$Cl$_2$ 10:90). 1HNMR (CD$_3$OD:acetone-d6 3:1, 500 MHz) δ 4.66 (s br, 1 H), 4.61 (d, J=4.4 Hz, 0.33 H, —H1), 4.54 (s br, 1 H), 4.35 (d, J=9.0 Hz, 0.67 H, β-H1), 4.06 (s br, 0.67 H, β), 4.04-4.02 (m, 0.33 H, α), 3.98-3.96 (m, 0.33 H, α), 3.85-3.81 (m, 0.33 H, α), 3.65-3.62 (m, 0.67 H, β), 3.61-3.59 (m, 0.67 H, β), 3.58-3.54 (m, 2.33 H, α), 3.53 (s, 3 H), 3.51-3.49 (m, 0.67 H, β), 3.47-3.46 (m, 0.33H, a), 3.44-3.42 (m, 0.67 H, β), 2.98 (td, J=10.7, 4.8 Hz, 1 H), 2.27 (td, J=12.8, 3.2 Hz, 1 H), 2.19-2.16 (m, 1 H), 1.90-1.83 (m, 2 H), 1.69-1.55 (m, 7 H), 1.52-1.30 (m, 12 H), 1.19 (dd, J=12.5, 4.3 Hz, 1 H), 1.14-1.11 (m, 1 H), 1.04-1.01 (m, 1 H), 0.98 (s, 3 H), 0.92 (s, 3 H), 0.86 (s br, 1 H), 0.83 (s, 6 H), 0.78 (s, 3 H); 13C NMR (CD$_3$OD:acetone-d6 3:1, 125 MHz) δ 179.14, 171.90, 151.85, 110.14, 100.18 (α-C1), 91.18 (β-C1), 85.07 (α), 72.86 (α), 72.33 (β), 72.10 (α), 68.73 (β), 68.22 (β), 65.70, 63.65 (α), 62.58 (β), 61.85, 58.14, 57.35, 57.19, 51.70, 50.22, 48.29, 43.46, 41.75, 40.40, 39.39, 39.01, 38.17, 37.92, 35.33, 33.15, 31.58, 30.70, 29.04, 26.67, 23.40, 21.92, 19.55, 16.96, 16.64, 16.60, 15.13, 9.12; HRMS (ESI) m/z for $C_{38}H_{62}N_2O_8$ ([M+H]+) 675.4594, calc. 675.4579.

Example 11

Synthesis of (3S)-O-(N-Methoxy-N-β-D-allosylglycyl)betulinic acid (BA1)

Using aglycon 7 (31 mg, 0.057 mmol), the product was yielded as a white solid (9 mg, 23%, Rf=0.35 MeOH:$CH_2Cl_2$ 10:90). 1H NMR ($CD_3OD$, 500 MHz) δ 4.75 (s br, 1 H), 4.63 (s br, 1 H), 4.62-4.59 (m, 1 H), 4.50 (d, J=9.2 Hz, 1 H), 4.12 (t, J=2.9 Hz, 1 H), 3.87-3.83 (m, 2 H), 3.72 (s, 2 H), 3.69 (s, 3 H), 3.60-3.56 (m, 1 H), 3.55-3.51 (m, 1 H), 3.50-3.46 (m, 1 H), 3.06 (td, J=10.9, 4.7 Hz, 1 H), 2.36 (td, J=12.7, 3.3 Hz, 1 H), 2.27 (dt, J=12.7, 3.1 Hz, 1 H), 1.98-1.91 (m, 2 H), 1.80-1.63 (m, 10 H), 1.62-1.55 (m, 2 H), 1.53-1.39 (m, 8 H), 1.29-1.26 (m, 1 H), 1.12 (dd, J=13.1, 4.2 Hz, 1 H), 1.06 (s, 3 H), 1.02 (s, 3 H), 0.94 (s, 3 H), 0.92 (s, 6 H), 0.91-0.87 (m, 1 H); HRMS (ESI) m/z for $C_{39}H_{63}NNaO_{10}$ ([M+Na]+) 728.4365, calc. 728.4344.

Example 12

Synthesis of (3S)-O-(N-Methoxy-N-(3-L-allosylglycyl)betulinic acid (BA2)

Using aglycon 7 (31 mg, 0.057 mmol), the product was yielded as a white solid (8 mg, 20%, Rf=0.35 MeOH:$CH_2Cl_2$ 10:90). 1H NMR ($CD_3OD$, 500 MHz) δ 4.74 (s br, 1 H), 4.63 (s br, 1 H), 4.62-4.56 (m, 1 H), 4.50 (d, J=9.2 Hz, 1 H), 4.12 (t, J=2.9 Hz, 1 H), 3.92-3.83 (m, 2 H), 3.72 (s, 2 H), 3.69 (s, 3 H), 3.60-3.56 (m, 1 H), 3.55-3.51 (m, 1 H), 3.50-3.46 (m, 1 H), 3.07 (td, J=10.9, 4.7 Hz, 1 H), 2.36 (td, J=12.6, 3.3 Hz, 1 H), 2.27 (dt, J=12.6, 3.2 Hz, 1 H), 1.98-1.93 (m, 2 H), 1.80-1.63 (m, 10 H), 1.62-1.54 (m, 2 H), 1.53-1.39 (m, 8 H), 1.30-1.25 (m, 1 H), 1.14 (dd, J=13.1, 4.2 Hz, 1 H), 1.06 (s, 3 H), 1.02 (s, 3 H), 0.94 (s, 3 H), 0.92 (s, 6 H), 0.91-0.87 (m, 1 H); HRMS (ESI) m/z for $C_{39}H_{63}NNaO_{10}$ ([M+Na]+) 728.4382, calc. 728.4344.

Example 13

Synthesis of (3S)-O-(N-Methoxy-N-D-fucosylglycyl)betulinic acid (BA8)

Using aglycon 7 (33 mg, 0.061 mmol), the anomeric mixture was yielded as a white solid (8 mg, 19%, Rf=0.28 MeOH:$CH_2Cl_2$ 5:95). 1H NMR ($CD_3OD$, 500 MHz) δ 4.71 (s br, 1 H), 4.59 (s br, 1 H), 4.58-4.54 (m, 1 H), 4.48 (d, J=5.2 Hz, 0.33 H, α-H1), 4.14 (t, J=5.2 Hz, 0.33 H, α), 4.08 (d, J=8.6 Hz, 0.67H, β-H1), 3.94 (dd, J=7.6, 6.2 Hz, 0.33 H, α), 3.78-3.72 (m, 1 H, α+β), 3.66 (s, 2 H), 3.64-3.62 (m, 0.33 H, α), 3.60 (s, 3 H), 3.59-3.58 (m, 0.67 H, β), 3.51-3.47 (m, 1.34 H, 2β), 3.02 (td, J=10.7, 4.8 Hz, 1 H), 2.31 (td, J=12.7, 3.3 Hz, 1 H), 2.23 (dt, J=12.7, 3.2 Hz, 1 H), 1.95-1.87 (m, 2 H), 1.78-1.60 (m, 10 H), 1.59-1.50 (m, 2 H), 1.49-1.36 (m, 7 H), 1.31-1.28 (m, 1 H), 1.25 (d, J=6.4 Hz, 2 H, α-H6), 1.23 (d, J=6.6 Hz, 1 H, β-H6), 1.21-1.15 (m, 1H), 1.09 (dd, J=12.9, 4.4 Hz, 1 H), 1.02 (s, 3 H), 0.98 (s, 3 H), 0.91 (s, 3 H), 0.88 (s, 6 H), 0.87-0.83 (m, 1H); HRMS (ESI) m/z for $C_{39}H_{63}NNaO_9$ ([M+Na]+) 712.4409, calc. 712.4395.

Example 14

Synthesis of (3S)-O-(N-Methoxy-N-L-fucosylglycyl)betulinic acid (BA9)

Using aglycon 7 (36 mg, 0.061 mmol), the anomeric mixture was yielded as a white solid (6 mg, 13%, Rf=0.28 MeOH:CH2Cl2 5:95). 1H NMR (CD3OD, 500 MHz) δ 4.71 (s br, 1 H), 4.59 (s br, 1 H), 4.57-4.53 (m, 1 H), 4.51 (d, J=5.2 Hz, 0.33 H, α-H1), 4.14 (t, J=5.2 Hz, 0.33 H, α), 4.10 (d, J=8.6 Hz, 0.67 H, β-H1), 3.94 (dd, J=7.5, 6.3 Hz, 0.33 H, α), 3.78-3.72 (m, 1 H, α+β), 3.66 (s, 2 H), 3.64-3.62 (m, 0.33 H, α), 3.60 (s, 3 H), 3.59-3.58 (m, 0.67 H, β), 3.51-3.47 (m, 1.34 H, 2β), 3.02 (td, J=10.7, 4.8 Hz, 1 H), 2.31 (td, J=12.7, 3.2 Hz, 1 H), 2.23 (dt, J=12.7, 3.2 Hz, 1 H), 1.95-1.86 (m, 2 H), 1.78-1.59 (m, 10 H), 1.59-1.50 (m, 2 H), 1.49-1.35 (m, 7 H), 1.31-1.27 (m, 1 H), 1.25 (d, J=6.4 Hz, 2 H, α-H6), 1.23 (d, J=6.6 Hz, 1 H, β-H6), 1.21-1.15 (m, 1 H), 1.07 (dd, J=12.9, 4.4 Hz, 1 H), 1.02 (s, 3 H), 0.98 (s, 3 H), 0.90 (s, 3 H), 0.88 (s, 6 H), 0.87-0.83 (m, 1 H); HRMS (ESI) m/z for C39H61NO9 ([M−H]−) 688.4423, calc. 688.4430.

Example 15

Synthesis of (3S)-O-(N-Methoxy-N-(3-deoxy-D-glucosyl)glycyl)betulinic acid (BA17)

Using aglycon 7 (31 mg, 0.057 mmol), the anomeric mixture was yielded as a white solid (7 mg, 18%, Rf=0.20 MeOH:$CH_2Cl_2$ 5:95). 1H NMR (CD3OD, 500 MHz) δ 4.74 (s br, 1 H), 4.63 (s br, 1 H), 4.57 (dd, J=11.3, 5.0 Hz, 1 H), 4.54 (d, J=1.4 Hz, 0.25H, α-H1), 4.42 (d, J=5.7 Hz, 0.75 H, α-H1), 4.28-4.20 (m, 1 H, α+β), 4.09 (dd, J=8.9, 2.6 Hz, 0.25 H, β), 3.88-3.84 (m, 0.25 H, β), 3.72 (s, 2 H), 3.70-3.65 (m, 1.5 H, 2β), 3.62-3.50 (m, 2 H, 2α+2β), 3.07 (td, J=10.9, 4.8 Hz, 1 H), 2.36 (td, J=12.8, 3.3 Hz, 1 H), 2.27 (dt, J=12.8, 3.2 Hz, 1 H), 2.21-2.15 (m, 1 H, α+β), 1.98-1.90 (m, 3 H), 1.80-1.63 (m, 10 H), 1.60-1.54 (m, 2 H), 1.53-1.39 (m, 7 H), 1.36-1.28 (m, 1 H), 1.24-1.18 (m, 1 H), 1.11 (dd, J=13.1, 4.4 Hz, 1 H), 1.06 (s, 3 H), 1.02 (s, 3 H), 0.94 (s, 3 H), 0.92 (s, 6 H), 0.90-0.86 (m, 1 H); HRMS (ESI) m/z for C39H63NNaO9 ([M+Na]+) 712.4434, calc. 712.4395.

Example 16

Synthesis of (3S)-O-(N-Methoxy-N-(6-deoxy-(β-D-glucosyl)glycyl)betulinic acid (BA18)

Using aglycon 7 (31 mg, 0.057 mmol), the product was yielded as a white solid (3 mg, 8%, Rf=0.16 MeOH:$CH_2Cl_2$ 5:95). 1H NMR (CD3OD, 500 MHz) δ 4.74 (s br, 1 H), 4.62 (s br, 1 H), 4.61-4.58 (m, 1 H), 4.12 (d, J=8.9 Hz, 1 H), 3.72 (s, 2 H), 3.66 (s, 3 H), 3.39-3.35 (m, 2 H), 3.29 (dd, J=9.3, 6.1 Hz, 1 H), 3.07 (td, J=10.7, 4.7 Hz, 1 H), 3.00 (t, J=9.1 Hz, 1 H), 2.40-2.33 (m, 1 H), 2.29-2.25 (m, 1 H), 1.98-1.90 (m, 2 H), 1.80-1.62 (m, 10 H), 1.60-1.54 (m, 2 H), 1.53-1.39 (m, 7 H), 1.36-1.32 (m, 1 H), 1.30 (d, J=6.1 Hz, 3 H), 1.24-1.18 (m, 1 H), 1.11 (m, 1 H), 1.06 (s, 3 H), 1.02 (s, 3 H), 0.94 (s, 3 H), 0.92 (s, 6 H), 0.90-0.86 (m, 1 H); HRMS (ESI) m/z for C39H63NNaO9 ([M+Na]+) 712.4420, calc. 712.4395.

Example 17

Synthesis of (3S)-O-(N-Methoxy-N-β-L-xylosylglycyl)betulinic acid (BA32)

Using aglycon 7 (33 mg, 0.061 mmol), the product was yielded as a white solid (11 mg, 27%, Rf=0.19 MeOH:

CH$_2$Cl$_2$ 5:95). 1H NMR (CD3OD, 500 MHz) 4.74 (s br, 1 H), 4.62 (s br, 1 H), 4.60-4.58 (m, 1 H), 4.11 (d, J=8.3 Hz, 1 H), 3.91 (dd, J=11.2, 5.4 Hz, 1 H), 3.78-3.76 (m, 1 H), 3.66 (s, 2 H), 3.64 (s, 3 H), 3.52-3.45 (m, 1 H), 3.38-3.36 (m, 1 H), 3.18 (t, J=11.0 Hz, 1 H), 3.05 (td, J=10.8, 4.6 Hz, 1 H), 2.33 (td, J=12.7, 3.2 Hz, 1 H), 2.27 (dt, J=12.7, 2.9 Hz, 1 H), 1.99-1.90 (m, 2 H), 1.80-1.61 (m, 10 H), 1.61-1.53 (m, 2 H), 1.52-1.37 (m, 7 H), 1.33-1.28 (m, 1 H), 1.24-1.17 (m, 1 H), 1.10 (dd, J=13.3, 4.2 Hz, 1 H), 1.05 (s, 3 H), 1.00 (s, 3 H), 0.92 (s, 3 H), 0.90 (s, 6 H), 0.88-0.85 (m, 1H); HRMS (ESI) m/z for C39H60NO9 ([M−H]−) 674.4273, calc. 674.4274.

Example 18

Synthesis of (3S)-N-(N'-Methoxy-N'-β-D-altrosylglycyl)betulinic acid (ABA1)

Using aglycon 10 (47 mg, 0.087 mmol), the product was yielded as a white solid (12 mg, 20%, Rf=0.25 MeOH:CH2Cl2 10:90). 1H NMR (CD3OD:acetone-d6 3:1, 500 MHz) δ 4.74 (s br, 1 H), 4.63 (s br, 1 H), 4.55 (d, J=4.6 Hz, 1 H), 4.22 (t, J=5.9 Hz, 1 H), 4.17 (q, J=5.0 Hz, 1 H), 3.98-3.93 (m, 2 H), 3.87-3.78 (m, 1 H), 3.76-3.68 (m, 3 H), 3.66 (s, 3 H), 3.07 (td, J=10.7, 4.6 Hz, 1 H), 2.36 (td, J=12.7, 3.1 Hz, 1 H), 2.27 (dt, J=12.7, 3.2 Hz, 1 H), 1.98-1.91 (m, 2 H), 1.79-1.63 (m, 7 H), 1.62-1.40 (m, 12 H), 1.33-1.29 (m, 1 H), 1.24-1.21 (m, 1 H), 1.16-1.11 (m, 1 H), 1.07 (s, 3 H), 1.01 (s, 3 H), 0.95 (s br, 1 H), 0.92 (s, 6 H), 0.87 (s, 3 H); HRMS (ESI) m/z for C39H65N2O9 ([M+H]+) 705.4686, calc. 705.4685.

Example 19

Synthesis of (3S)-N-(N'-Methoxy-N'-D-xylosylglycyl)betulinic acid (ABA5)

Using aglycon 10 (48 mg, 0.088 mmol), the product was yielded as a white solid (45 mg, 75%, Rf=0.35 MeOH:CH2Cl$_2$ 5:95). 1H NMR (CD3OD:acetone-d6 3:1, 500 MHz) δ 4.75 (s br, 1 H), 4.63 (s br, 1 H), 4.11 (d, J=8.7 Hz, 1 H), 3.90 (dd, J=11.1, 5.5 Hz, 1 H), 3.70-3.59 (m, 6 H), 3.51-3.46 (m, 1 H), 3.37 (t, J=8.9 Hz, 1H), 3.20 (t, J=10.9 Hz, 1 H), 3.07 (td, J=10.7, 4.6 Hz, 1 H), 2.36 (td, J=12.7, 3.2 Hz, 1 H), 2.27 (dt, J=12.7, 3.1 Hz, 1 H), 2.00-1.90 (m, 2 H), 1.80-1.63 (m, 7 H), 1.62-1.38 (m, 12 H), 1.34-1.26 (m, 1 H), 1.25-1.22 (m, 1 H), 1.14-1.10 (m, 1 H), 1.07 (s, 3 H), 1.01 (s, 3 H), 0.95 (s, 1 H), 0.92 (s, 3 H), 0.90 (s, 3 H), 0.87 (s, 3 H); HRMS (ESI) m/z for C38H61N2O8 ([M−H]−) 673.4435, calc. 673.4433.

Example 20

Cytotoxicity Assays

Testing was performed by the Keck-UWCCC Small Molecule Screening Facility (Madison, Wis.). Carcinoma cell lines were maintained and harvested as previously reported, along with compound handling and assay set up.[21] Cells were plated in 50 μL volumes in 384-well clear bottom tissue culture plates. Serial dilutions of 30 mM DMSO compound stock solutions were done in 96-well plates using a BioTek Precision XS liquid handler (Winooski, Vt.) to a concentration 100× greater than that of the most dilute assay. Final dilutions were performed in a 384-well plate in quadruplicate using a Beckman-Coulter Biomek FX liquid handler with a 384 channel pipetting head (Fullerton, Calif.) and were stored at −20° C. when not in use. Compounds were then added to the culture plates by the Biomek FX handler and were incubated at 37° C. for 72 h. The calcein AM reagent (acetoxymethyl ester; 30 μL, 10 μM) was then added, the cells were incubated for 30 m at 37° C., and plates were read for fluorescent emission (535 nm). Cell titer-glo reagent (15 μL; Promega Corp., Madison, Wis.) was added and the plates incubated for 10 m at room temperature with gentle agitation to lyse the cells. Each plate was reexamined for luminescence to verify inhibition. IC50 values for cytotoxicity were determined using XLfit 4.2 as previously reported.[21]

Example 21

Anti-HIV-1 Assay

Testing was performed by Southern Research Institute (Frederick, Md.) as previously described.[22] HIV-1 virus (IIIB strain) was pre-titered with CEM-SS lymphocytes such that control wells exhibited 70 to 95% loss of cell viability six days after infection due to viral replication. Both cells and virus were mixed with compound (10 μM & 1 μM for ABA1-5 and 10 or 10 μM for all others) in triplicate in 96-well plates and incubated for six days at 37° C. Compound cytoprotection and cytotoxicity were evaluated using MTS tetrazolium dye (Promega Corp., Madison, Wis.) as previously reported.[23] Each assay plate used the following controls: cells only, cells/virus, cells/compound, compound only. The reverse transcriptase inhibitor AZT and protease inhibitor Indinavir were included as positive controls.

Example 22

Methods of Use

In use, the enhanced neoglycoside of the present invention may be used to treat patients suffering from HIV by administering to the patient a therapeutically effective amount of the enhanced neoglycoside. The enhanced neoglycosides of the present invention may also be used to treat patients suffering from cancer by administering to the patient a therapeutically effective amount of the enhanced neoglycoside.

By "patient" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a neoglycoside of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The neoglycoside of the present invention, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques. The neoglycoside according to the present invention may also contain adjuvants such as preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the neoglycosides of the present invention can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions for rectal or vaginal administration can be prepared by mixing a neoglycoside of the present invention and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the neoglycoside. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a neoglycoside according to the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the neoglycosides of the present invention may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The neoglycosides of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the neoglycoside is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the neoglycoside of the present invention.

By "cancer" we mean all cancers and neoplastic disorders including but not limited to acute leukemia, acute t-cell leukemia, acute lymphocytic leukemia, acute myelocytic leukemia, myeloblastic, promyelocytic, myelomonocytic, Monocytic, erythroleukemia, chronic leukemia, chronic myelocytic (granulocytic) leukemia, chronic lymphocytic leukemia, Polycythemia vera, Hodgkin's disease, non-Hodgkin's disease, Multiple myeloma, Waldenstrom's macroglobulinemia, Heavy chain disease, Solid tumors, sarcomas, and carcinomas including fibrosarcoma, myxosarcoma, liposarcoma, chondrosarcoma, osteogenic sarcoma, chordoma angiosarcoma, endotheliosarcoma, lymphangiosarcoma, lymphangioendotheliosarcoma, synovioma mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES (1) (a) Kren, V.; Řezanka, T. *FEMS Microbiol. Rev.* 2008, 32, 858-889; (b) Thorson, J. S.; Hosted, T. J., Jr.; Jiang, J.; Biggins, J. B.; Ahlert, J. *Curr. Org. Chem.* 2001, 5, 139-167. (c) Weymouth-Wilson, A. C. *Nat. Prod. Rep.* 1997, 14, 99-110.

(2) Ahmed, A.; Peters, N. R.; Fitzgerald, M. K.; Watson, J. A., Jr.; Hoffmann, F. M.; Thorson, J. S. *J. Am. Chem. Soc.* 2006, 128, 14224-14225.

(3) Ghiorghis, A.; Talebian, A.; Clarke, R. *Cancer Chemother. Pharmacol.* 1992, 29, 290-296.

(4) Imbert, T. F. *Biochimie* 1998, 80, 207-222.

(5) Abel, M.; Szweda, R.; Trepanier, D.; Yatscoff, R. W.; Foster, R. T. Rapamycin Carbohydrate Derivatives. U.S. Pat. No. 7,160,867, Jan. 9, 2007. Steiner, H. H.; Pietsch, T.; Debatin, K.-M. *Int. J. Cancer* 1999, 82, 435-441. (c) Chintharlapalli, S.; Papineni, S.; Ramaiah, S. K.; Safe, S. *Cancer Res.* 2007, 67, 2816-2823.

(6) Liu, D.; Sinchaikeul, S.; Reddy, P. V. G.; Chang, M.; Chen, S. *Bioorg. Med. Chem. Lett.* 2007, 17, 617-620.

(7) (a) Salas, J. A.; Mé ndez, C. *Trends Microbiol.* 2007, 15, 119-232. (b) Thibodeaux, C. J.; Melanc,on, C. E.; Liu, H. *Nature* 2007, 446, 1008-1016. (c) Blanchard, S.; Thorson, J. S. *Curr. Opin. Chem. Biol.* 2006, 10, 263-271. (d) Griffith, B. R.; Langenhan, J. M.; Thorson, J. S. *Curr. Opin. Biotechnol.* 2005, 16, 622-630. (e) Langenhan, J. M.; Griffith, B. R.; Thorson, J. S. *J. Nat. Prod.* 2005, 68, 1696-1711.

(8) (a) Peri, F.; Dumy, P.; Mutter, M. *Tetrahedron* 1998, 54, 12269-12278. (b) Peri, F.; Deutman, A.; La Ferla, B.; Nicotra, F. *Chem. Commun.* 2002, 1504-1505. (c) Carrasco, M. R.; Nguyen, M. J.; Burnell, D. R.; MacLaren, M. D.; Hengel, S. M. *Tetrahedron Lett.* 2002, 43, 5727-5729. (d) Carrasco, M. R.; Brown, R. T. *J. Org. Chem.* 2003, 68, 8853-8858. (e) Carrasco, M. R.; Brown, R. T.; Serafimova, I. M.; Silva, O. *J. Org. Chem.* 2003, 68, 195-197. (f) Peri, F. *MinireV. Med. Chem.* 2003, 3, 658-665. (g) Peri, F.; Jimé nez-Barbero, J.; Garcî a-Aparicio, V.; Tvaroska, I.; Nicotra, F. *Chem. Eur. J.* 2004, 10, 1433-1444. (h) Peri, F.; Nicotra, F. *Chem. Commun.* 2004, 623-627. (i) Langenhan, J. M.; Thorson, J. S. *Curr. Org. Synth.* 2005, 2, 59-81. (j) Carrasco, M. R.; Brown, R. T.; Doan, V. H.; Kandel, S. M.; Lee, F. C. *Biopolymers* 2006, 84, 414-420. (k) Nicotra, F.; Cipolla, L.; Peri, F.; La Ferla, B.; Redaelli, C. *AdV. Carb. Chem. Biochem.* 2008, 61, 363-410.

(9) (a) Langenhan, J. M.; Peters, N. R.; Guzei, I. A.; Hoffman, M. A.; Thorson, J. S. *Proc. Natl. Acad. Sci. U.S.A.* 2005, 102, 12305-12310. (b) Griffith, B. R.; Krepel, C.; Fu, X.; Blanchard, S.; Ahmed, A.; Edmiston, C. E.; Thorson, J. S. *J. Am. Chem. Soc.* 2007, 129, 8150-8155. (c) Langenhan, J.

M.; Engle, J. M.; Slevin, L. K.; Fay, L. R.; Lucker, R. W.; Smith, K. R.; Endo, M. M. *Bioorg. Med. Chem. Lett.* 2008, 18, 670-673.
(10) (a) Langenhan, J. M.; Peters, N. R.; Guzei, I. A.; Hoffman, M. A.; Thorson, J. S. *Proc. Nat. Acad. Sci. U.S.A.* 2005, 102, 12305-12310. (b) Griffith, B. R.; Krepel, C.; Fu. X.; Blanchard, S.; Ahmed, A.; Edmiston, C. E.; Thorson, J. S. *J. Am. Chem. Soc.* 2007, 129, 8150-8155. (c) Langenhan, J. M.; Engle, J. M.; Slevin, L. K.; Fay, L. R.; Lucker, R. W.; Smith, K. R.; Endo, M. M. *Bioorg. Med. Chem. Lett.* 2008, 18, 670-673.
(11) (a) Deorukhkar, A.; Krishnan, S.; Sethi, G.; Aggarwal, B. B. *Exp. Opin. Inv. Drugs* 2007, 16, 1753-1773. (b) Butler, M. S. *Nat. Prod. Rep.* 2008, 25, 475-516. (c) Udenigwe, C. C.; Ramprasath, V. R.; Aluko, R. E.; Jones, P. J. H. *Nutr. Rev.* 2008, 8, 445-454. (d) Saladino, R.; Gualandi, G.; Farina, A.; Crestini, C.; Nencioni, L.; Palamara, A. T. *Curr. Med. Chem.* 2008, 15, 1500-1519.
(12) For reviews see: (a) Cichewicz, R. H.; Kouzi, S. A. *Med. Res. Rev.* 2004, 24, 90-114. (b) Yogeeswari, P.; Sriram, D. *Curr. Med. Chem.* 2005, 12, 657-666. (c) Sami, A.; Tam, M.; Salme, K.; Jari, Y.-K. *Eur. J. Pharm. Sci.* 2006, 29, 1-13. (d) Fulda, S. *Int. J. Mol. Sci.* 2008, 9, 1096-1107.
(13) (a) Schmidt, M. L.; Kuzmanoff, K. L.; Ling-Indeck, L.; Pezzuto, J. M. *Eur. J. Cancer* 1997, 33, 2007-2010. (b) Fulda, S.; Jeremias, I.;
(14) (a) Li, F.; Goila-Gaur, R.; Salzwedel, K.; Kilgore, N. R.; Reddick, M.; Matallana, C.; Castillo, A.; Zoumplis, D.; Martin, D. E.; Orenstein, J. M.; Allaway, G. P.; Freed, E. O.; Wild, C. T. *Proc. Nat. Acad. Sci. U.S.A.* 2003, 100, 13555-13560. (b) Aiken, C.; Chen, C. H. *Trends Mol. Med.* 2005, 11, 31-36.
(15) (a) Kim, D. S. H. L.; Pezzuto, J. M.; Pisha, E. *Bioorg. Med. Chem. Lett.* 1998, 8, 1707-1712. (b) Kashiwada, Y.; Chiyo, J.; Ikeshiro, Y.; Nagao, T.; Okabe, H.; Cosentino, L. M.; Fowke, K.; Lee, K. H. *Bioorg. Med. Chem. Lett.* 2001, 11, 183-185.
(16) (a) Gauthier, C.; Legault, J.; Lebrun, M.; Dufour, P.; Pichette, A. *Bioorg. Med. Chem.* 2006, 14, 6713-6725. (b) Thibeault, D.; Gauthier, C.; Legault, J.; Bouchard, J.; Dufour, P.; Pichette, A. *Bioorg. Med. Chem.* 2007, 15, 6144-6157. Carrasco, M. R.; Brown, R. T.; Serafimova, I. M.; Silva, O. *J. Org. Chem.* 2003, 68, 195-197. (f) Peri, F. *Minirev. Med. Chem.* 2003, 3, 658-665. (g) Peri, F.; Jiménez-Barbero, J.; Garcia-Aparicio, V.; Tvaroška, I.; Nicotra, F. *Chem. Eur. J.* 2004, 10, 1433-1444. (h) Peri, F.; Nicotra, F. *Chem. Commun.* 2004, 623-627. (i) Langenhan, J. M.; Thorson, J. S. *Curr. Org. Syn.* 2005, 2, 59-81. (j) Carrasco, M. R.; Brown, R. T.; Doan, V. H.; Kandel, S. M.; Lee, F. C. *Biopolymers* 2006, 84, 414-420. (k) Nicotra, F.; Cipolla, L.; Peri, F.; La Ferla, B.; Redaelli, C. *Adv. Carb. Chem. Biochem.* 2008, 61, 363-410.
(17) Kim, D. S. H. L.; Chen, Z.; Nguyen, V. T.; Pezzuto, J. M.; Qiu, S.; Lu, Z.-Z. *Synth. Commun.* 1997, 27, 1607-1612.
(18) Kashiwada, Y.; Chiyo, J.; Ikeshiro, Y.; Nagao, T.; Okabe, H.; Cosentino, L. M.; Fowke, K.; Morris-Natschke, S. L.; Lee, K.-H. *Chem. Pharm. Bull.* 2000, 48, 1387-1390.
(19) Kim, D. S. H. L.; Pezzuto, J. M.; Pisha, E. *Bioorg. Med. Chem. Lett.* 1998, 8, 1707-1712.
(20) Ahmed, A.; Peters, N. R.; Fitzgerald, M. K.; Watson, J. A., Jr.; Hoffman, F. M.; Thorson, J. S. *J. Am. Chem. Soc.* 2006, 128, 14224-14225.
(21) Langenhan, J. M.; Peters, N. R.; Guzei, I. A.; Hoffman, M. A.; Thorson, J. S. *Proc. Nat. Acad. Sci. U.S.A.* 2005, 102, 12305-12310.
(22) Ptak, R. G.; Gallay, P. A.; Jochmans, D.; Halestrap, A. P.; Ruegg, U. T.; Pallansch, L. A.; Bobardt, M. D.; de Bethune, M.-P.; Neyts, J.; De Clercq, E.; Dumont, J.-M.; Scalfaro, P.; Besseghir, K.; Wenger, R. M.; Rosenwirth, B. *Antimicrob. Agents Chemother.* 2008, 52, 1302-1317.
(23) CellTiter 96 Aqueous One Solution Cell Proliferation Assay; Technical Bulletin TB245; Promega Corp.: Madison, Wis., December 2007.

We Claim:

1. A neoglycoside having the chemical structure:

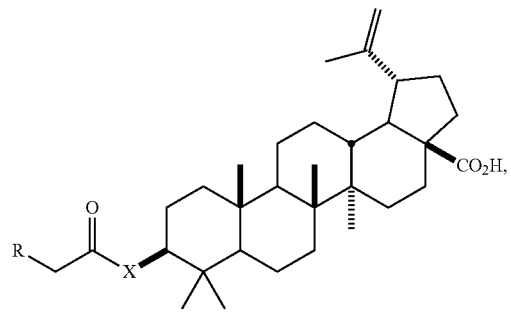

wherein X represents either O or NH, and wherein R is an amine group having the nitrogen atom covalently bonded to both a methoxy moiety ($CH_3O-$) and a reducing sugar.

2. The neoglycoside of claim 1, wherein R is chosen from the group consisting of:

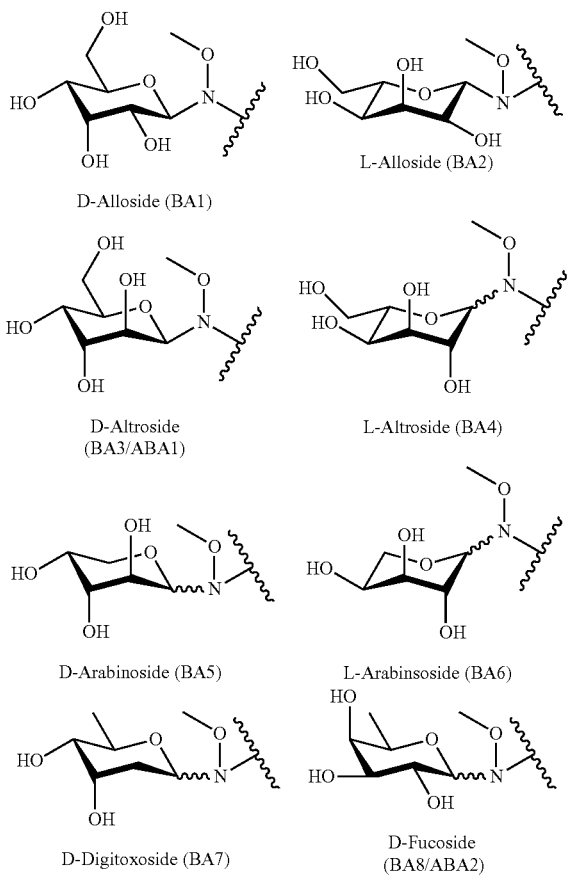

-continued

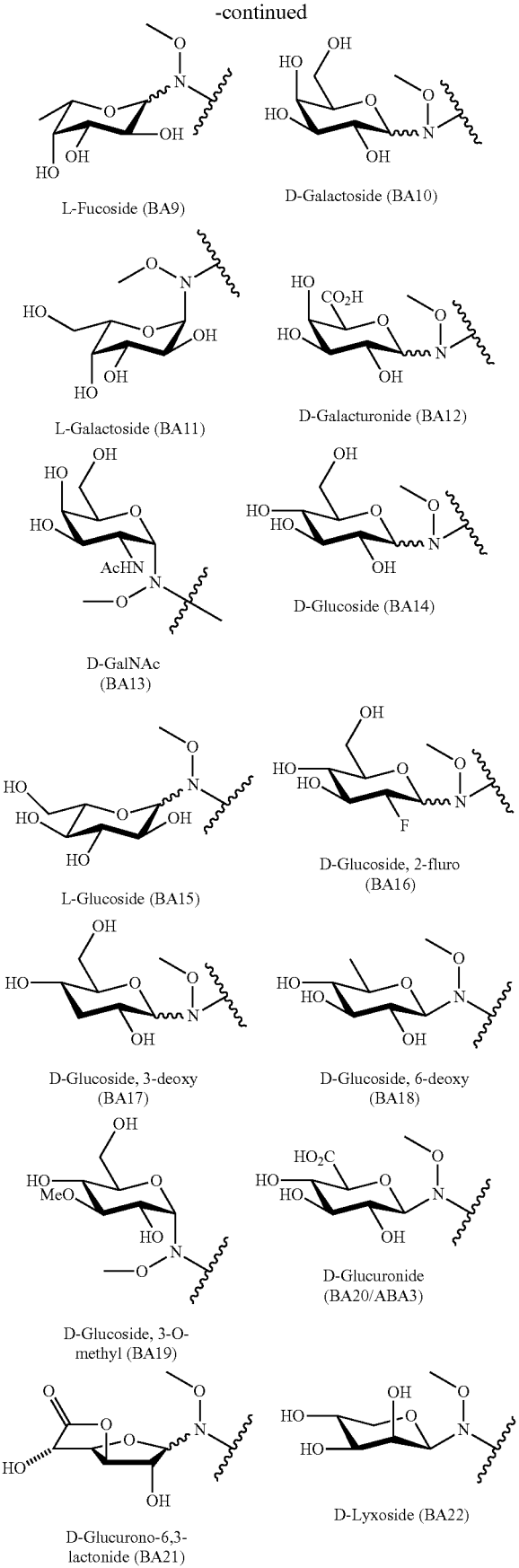

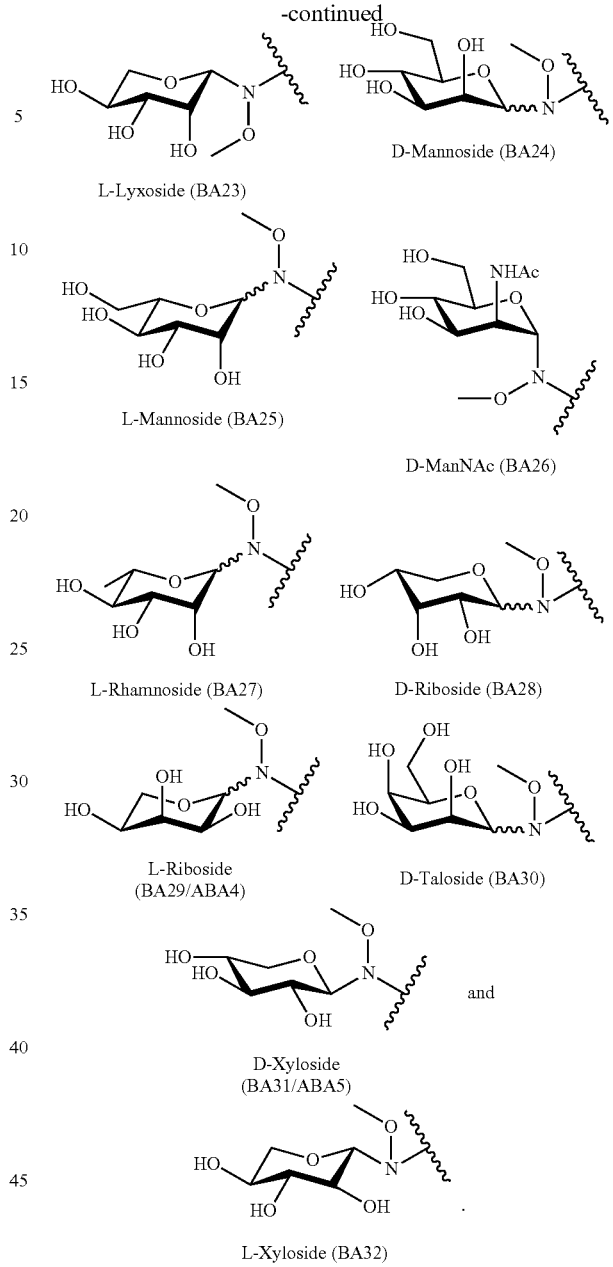

3. The neoglycoside as described by claim 1, wherein X represents an oxygen atom.

4. A library of neoglycosides comprising at least two of the neoglycosides described by claim 1.

5. A composition comprising one or more of the neoglycosides described by claim 1, or a pharmaceutically acceptable salt, or ester thereof, and a pharmaceutically acceptable carrier.

6. A method of treating a subject having cancer cells comprising the step of contacting the cancer cells with an effective amount of the neoglycoside as described by claim 1, or a pharmaceutically acceptable salt, or ester thereof, whereby the cancer cells are treated.

7. The method of claim 6, wherein the step of contacting the cancer cells with an effective amount of the neoglycoside, pharmaceutically acceptable salt, or ester thereof is accomplished by administering to the subject the composition described by claim 5.

8. A method of treating HIV infection comprising the step of administering to a subject having an HIV infection an effective amount of the neoglycoside as described in claim 1, or a pharmaceutically acceptable salt, or ester thereof.

9. The method of claim 8, wherein the step of administering an effective amount of the neoglycoside, pharmaceutically acceptable salt, or ester thereof is accomplished by administering to the subject the composition described by claim 5.

10. A method of making a neoglycoside comprising the steps of:
    (a) contacting a compound having a hydroxyl group with chloroacetyl chloride, DMAP, iodide ion, and methoxyamine (MeOHN$_2$) to produce an aglycon; and
    (b) contacting the aglycon produced in step (a) with one or more reducing sugars.

11. The method of claim 10, wherein the compound is betulinic acid.

12. The method described by claim 10, wherein the reducing sugar is D-allose, L-allose, D-altrose, L-altrose, D-arabinose, L-arabinose, D-digitoxose, D-fucose, L-fucose, D-galactose, L-galactose, D-galacturone, D-GalNAc, D-glucose, L-glucose, 2-fluoro-D-glucose, 3-deoxy-D-glucose, 6-deoxy-D-glucose, 3-O-methyl-D-glucose, D-glucurone, D-glucurono-6,3-lacone, D-lyxose, L-lyxose, D-mannose, L-mannose, D-manNAc, L-rhamnose, D-ribose, L-ribose, D-talose, D-xylose, or L-xylose.

13. The method described by claim 10, wherein the contacting is performed at a temperature from about 40 degrees Celsius to about 60 degrees Celsius.

14. The method described by claim 10, wherein the step of contacting the aglycon produced in step (a) with one or more reducing sugars is performed in the presence of a mixture of Methanol and CH$_2$Cl$_2$.

15. The method of claim 14, wherein the ratio of Methanol to CH$_2$Cl$_2$ in the mixture is about 6:1.

16. A neoglycoside produced by the method described by claim 10.

* * * * *

UNITED STATES PATENT AND TRADEMARK OFFICE
CERTIFICATE OF CORRECTION

PATENT NO.         : 8,653,043 B2
APPLICATION NO.    : 13/143639
DATED              : February 18, 2014
INVENTOR(S)        : Randal D. Goff and Jon Scott Thorson It is certified that error appears in the above-identified patent and that said Letters Patent is hereby corrected as shown below:

In the Specification:

Col. 1, Lines 18-21
Please replace the paragraph under the STATEMENT REGARDING FEDERALLY SPONSORED RESEARCH with: -- This invention was made with government support under CA113297 awarded by the National Institutes of Health. The government has certain rights in the invention. --

Signed and Sealed this
Twenty-seventh Day of May, 2014

Michelle K. Lee
*Deputy Director of the United States Patent and Trademark Office*